(12) United States Patent
Coutard

(10) Patent No.: US 10,363,496 B2
(45) Date of Patent: Jul. 30, 2019

(54) METHOD FOR PURIFICATION OF MONOCLONAL ANTIBODIES

(71) Applicant: LABORATOIRE FRANCAIS DU FRACTIONNEMENT ET DES BIOTECHNOLOGIES, Les Ulis (FR)

(72) Inventor: Francois Coutard, Ales (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 94 days.

(21) Appl. No.: 15/508,577

(22) PCT Filed: Sep. 4, 2015

(86) PCT No.: PCT/EP2015/070298
§ 371 (c)(1),
(2) Date: Mar. 3, 2017

(87) PCT Pub. No.: WO2016/034726
PCT Pub. Date: Mar. 10, 2016

(65) Prior Publication Data
US 2017/0274299 A1 Sep. 28, 2017

(30) Foreign Application Priority Data
Sep. 5, 2014 (FR) .................. 14 58346

(51) Int. Cl.
*C07K 1/36* (2006.01)
*B01D 15/38* (2006.01)
(Continued)

(52) U.S. Cl.
CPC .......... *B01D 15/3809* (2013.01); *C07K 1/18* (2013.01); *C07K 1/22* (2013.01); *C07K 1/34* (2013.01);
(Continued)

(58) Field of Classification Search
None
See application file for complete search history.

(56) References Cited

U.S. PATENT DOCUMENTS 5,084,559 A   1/1992   Profy
5,260,373 A   11/1993  Profy et al.
(Continued)

FOREIGN PATENT DOCUMENTS

WO    90/04036 A1   4/1990
WO    95/17085 A1   6/1995
(Continued)

OTHER PUBLICATIONS

Robert L. Fahrner et al., "Industrial purification of pharmaceutical antibodies: development, operation, and validation of chromatography processes", Biotechnol Genet Eng Rev., vol. 18, pp. 301-327, Jul. 2001 (cited in ISR).
(Continued)

*Primary Examiner* — Michelle S Horning
(74) *Attorney, Agent, or Firm* — Young & Thompson

(57) ABSTRACT

Disclosed is a method for purification of monoclonal antibodies or of a fusion protein between the Fc segment of an antibody and a second polypeptide, including a) an affinity chromatography step on a resin having as a matrix a crosslinked methacrylate polymer gel, on which the protein A is grafted, b) a viral inactivation step, c) a chromatography step exchanging cations on a resin having a crosslinked agarose gel matrix, on which sulfonate groups ($-SO_3-$) are grafted using dextran-based spacer arms, d) a chromatography step exchanging anions on a hydrophilic membrane of polyethersulfone coated with a crosslinked polymer on which quaternary amine groups (Q) are grafted, and e) a nanofiltration step using a filter having an asymmetric polyethersulfone double membrane with a porosity of approximately 20 nm.

13 Claims, 14 Drawing Sheets

(51) Int. Cl.

| | |
|---|---|
| C07K 16/06 | (2006.01) |
| C07K 1/18 | (2006.01) |
| C07K 1/22 | (2006.01) |
| C07K 1/34 | (2006.01) |
| C12M 1/00 | (2006.01) |
| C07K 16/08 | (2006.01) |
| C07K 16/12 | (2006.01) |
| C12N 15/82 | (2006.01) |
| G01N 30/02 | (2006.01) |

(52) U.S. Cl.
CPC .............. *C07K 1/36* (2013.01); *C07K 16/065* (2013.01); *C07K 16/08* (2013.01); *C07K 16/1232* (2013.01); *C07K 16/1271* (2013.01); *C07K 16/1282* (2013.01); *C12M 47/12* (2013.01); *C12N 15/8258* (2013.01); *C07K 16/12* (2013.01); *C07K 2317/76* (2013.01); *C07K 2319/30* (2013.01); *G01N 30/02* (2013.01)

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,591,669 | A | 1/1997 | Krimpenfort et al. |
| 5,598,369 | A | 1/1997 | Chen et al. |
| 6,013,763 | A | 1/2000 | Braisted et al. |
| 6,150,584 | A | 11/2000 | Kucherlapati et al. |
| 6,399,750 | B1 | 6/2002 | Johansson |
| 7,709,209 | B2 | 5/2010 | Hober et al. |
| 9,556,258 | B2 * | 1/2017 | Nti-Gyabaah ........... C07K 1/36 |

FOREIGN PATENT DOCUMENTS

| | | |
|---|---|---|
| WO | 99/51642 A1 | 10/1999 |
| WO | 00/26357 A2 | 5/2000 |
| WO | 00/42072 A2 | 7/2000 |
| WO | 01/26455 A1 | 4/2001 |
| WO | 2004/029207 A2 | 4/2004 |
| WO | 2004/050847 A2 | 6/2004 |
| WO | 2004/063351 A2 | 7/2004 |
| WO | 2004/074455 A2 | 9/2004 |
| WO | 2005/033281 A2 | 4/2005 |
| WO | 2007/048077 A2 | 4/2007 |
| WO | 2007/106078 A2 | 9/2007 |
| WO | 2011/050071 A2 | 4/2011 |
| WO | 2012/041768 A1 | 4/2012 |
| WO | 2012/083425 A1 | 6/2012 |
| WO | 2013/009526 A1 | 1/2013 |
| WO | 2013/013193 A1 | 1/2013 |
| WO | 2013/177115 A2 | 11/2013 |

OTHER PUBLICATIONS

Hui F. Liu et al., "Recovery and purification process development for monoclonal antibody production", mAbs 2:5, pp. 480-499, Sep.-Oct. 2010 (cited in ISR).
Gerald M. Edelman et al., "The Covalent Structure of an Entire γG Immunoglobulin Molecule", Proc. Natl. Acad. USA, vol. 63, pp. 78-85, 1969 (cited in specification).
Robert L. Shields et al., "High Resolution Mapping of the Binding Site on Human IgG1 for FcγRI, FcγRII, FcγRIII, and FcRn and Design of IgG1 Variants with Improved Binding to the FcγR", J Biol Chem, vol. 276, No. 9, pp. 5591-6604, Mar. 2, 2001 (cited in specification).
Greg A. Lazar et al., "Engineered antibody Fc variants with enhanced effector function" Proc Natl Acad Sci, vol. 103, No. 11), pp. 4005-4010, Mar. 14, 2006 (cited in specification).
Esohe E. Idusogie et al. Engineered Antibodies with Increased Activity to Recruit Complement, J Immunol., 2001; vol. 166, pp. 2571-2575, 2001 (cited in specification).
William F. Dall'Acqua et al., "Modulation of the Effector Functions of a Human IgG1 through Engineering of It's Hinge Region" J Immunol 2006; vol. 177, pp. 1129-1138, 2006 (cited in specification).
Gregory L. Moore et al. "Engineered Fc variant antibodies with enhanced ability to recruit complement and mediate effector functions" mAbs 2:2, 1 pp. 181-189; Mar./Apr., 2010 (cited in specification).
Martine Verhoeyen et al. "Engineering of Antibodies", BioEssays, vol. 8, No. 2, pp. 74-78, Feb./Mar. 1988 (cited in specification).
Martine Verhoeyen et al. "Reshaping Human Antibodies: Grafting an Antilysozyme Activity", Science vol. 239, pp. 1534-1536, Mar. 25, 1988 (cited in specification).
Peter T. Jones et al. "Replacing the complementarity-determining regions in a human antibody with those from a mouse", Nature, vol. 321, pp. 522-525, May 29,1986 (cited in specification).
Lutz Riechmann et al., "Reshaping human antibodies for therapy", Nature, vol. 332, pp. 323-327, Mar. 24, 1988 (cited in specification).
Juan C. Almagro et al. "Humanization of antibodies", Frontiers in Bioscience 13, pp. 1619-1633, Jan. 1, 2008 (cited specification).
Aya Jakobovits et al., "Analysis of homozygous mutant chimeric mice: Deletion of the immunoglobulin heavy-chain joining region blocks B-cell development and antibody production", Proc. Natl. Acad. Sci. USA., vol. 90, pp. 2551-2555, Mar. 1993 (cited in specification).
Aya Jakobovits et al., "Germ-line transmission and expression of a human-derived yeast artificial chromosome", Nature, vol. 362, pp. 255-258, Mar. 18, 1993 (cited in specification).
Marianne Bruggemann et al., "Designer Mice: The Production of Human Antibody Repertoires in Transgenic Animals", Year in Immunol., vol. 7, pp. 33-40, (1993) (cited in specification).
Michel A. Duchosal et al. "Immunization of hu-PBL-SCID mice and the rescue of human monoclonal Fab fragments through combinational libraries", Nature, vol. 355, pp. 258-262, Jan. 16, 1992 (cited in specification).
Hennie R. Hoogenboom et al., By-passing Immunisation Human Antibodies from Synthetic Repertoires of Germline VH Gene Segments Rearranged in Vitro, J. Mol. Biol., vol. 227, pp. 381-388, (1992) (cited in specification).
James D. Marks et al., "By-passing Immunization Human Antibodies from V-gene Libraries Displayed on Phage", J. Mol. Biol., vol. 222, pp. 581-597 (1991) (cited in specification).
Tristan J. Vaughan et al. "Human Antibodies with Sub-nanomolar Affinities Isolated from a Large Non-immunized Phage Display Library", Nature Biotech, vol. 14, pp. 309-314, Mar. 1996 (cited in specification).
T. M. Ryan et al., "Knockout-Transgenic Mouse Model of Sickle Cell Disease", Science, vol. 278, pp. 873-876, Oct. 31, 1997 (cited in specification).
Jose B. Cibelli et al., "Cloned Transgenic Calves Produced from Nonquiescent Fetal Fibroblasts", Science, vol. 280, pp. 1256-1258, May 22, 1998 (cited in specification).
Eva Stoger et al., "Practical considerations for pharmaceutical antibody production in different crop systems", Molecular Breeding 9, pp. 149-158 (2002) (cited in specification).
Rainer Fischer et al., "Production of antibodies in plants and their use for global health", Vaccine 21, pp. 820-825 (2003) (cited in specification).
Donald N. Forthal et al., "Fc-Glycosylation Influences Fcγ Receptor Binding and Cell-Mediated Anti-HIV Activity of Monoclonal Antibody 2G12, The Journal of Inmmunology, vol. 185, pp. 6876-6882 (2010) (cited in specification).
Julian K-C. MA et al., "The Production of Recombinant Pharmaceutical Proteins in Plants", Nature Review, Genetics, vol. 4, pp. 794-805, Oct. 2003 (cited in specification).
Stefan Schillberg et al., "Opportunities for recombinant antigen and antibody expression in transgenic plants—technology assessment", Vaccine 23, pp. 1764-1769, (2005) (cited in specification).
Sven Lofdahl et al., "Gene for staphylococcal protein A", Proc Natl Acad Sci U S A., vol. 80, pp. 697-701, Feb. 1983 (cited in specification).
Mathias Uhlen et al. "Complete Sequence of the Staphylococcal Gene Encoding Protein A", J Biol Chem., vol. 259, No. 3, pp. 1695-1702, Feb. 10, 1984 (cited in specification).

(56) References Cited

OTHER PUBLICATIONS

EP Search Report, dated Jan. 26, 2016, from corresponding EP application.

* cited by examiner

METHOD FOR PURIFICATION OF MONOCLONAL ANTIBODIES

FIELD OF THE INVENTION

The present invention relates to the field of the methods for purification of monoclonal antibodies or fusion proteins intended for pharmaceutical applications. It relates to a method for purification of a monoclonal antibody or a fusion protein between the Fc fragment of an antibody and a second polypeptide, comprising a) an affinity chromatography step on a resin having as matrix a cross-linked methacrylate polymer gel, on which protein A is grafted, b) a viral inactivation step, c) a cation-exchange chromatography step on a resin having as matrix a cross-linked agarose gel, on which sulfonate groups ($-SO_3-$) are grafted via dextran-based spacer arms, d) an anion-exchange chromatography step on a hydrophilic polyethersulfone membrane coated with a cross-linked polymer on which quaternary amine groups (Q) are grafted, and e) a nanofiltration step with a filter having a dual polyethersulfone membrane having a pore size of about 20 nm.

PRIOR ART

We have witnessed during the last decade an intense development of passive immunotherapy treatments using antibodies, often monoclonal antibodies, in various therapeutic fields: cancers, prevention of alloimmunization in Rhesus-negative expectant mothers, infectious diseases, inflammatory diseases and particularly autoimmune diseases.

To be able to be used as a medicament, an antibody must meet stringent requirements in terms of quality, purity, and health safety. Consequently, various methods for purification of antibodies have been developed to meet these requirements. These methods generally involve several steps of chromatographic purification, as well as one or more viral clearance or inactivation steps (Fahrner et al. Biotechnol Genet Eng Rev. 2001; 18:301-27; Liu et al. MAbs. 2010 September-October; 2(5):480-99).

Although many methods for obtaining purified antibodies meeting the requirements of the health authorities have been disclosed, there exists nevertheless a need for optimized purification methods. Indeed, the existing methods impose significant production costs on manufacturers, which it is important to reduce to as much as possible in order to lower the cost of monoclonal antibody treatments.

The overall cost of an antibody production method varies as a function of a certain number of factors, such as in particular the cost of each product used for the purification, the quantity of antibodies that can be processed at one time, the time required for each step of the method, and the yield of each step of the method. Moreover, these factors are interdependent, i.e. the choice of a particular product for one of the purification steps will influence each of these factors differently.

However, for each purification step that can be used in a method for purification of a monoclonal antibody, the person skilled in the art must make a choice between numerous commercially-available products, each having its advantages and its disadvantages. Thus, in the context of a chromatographic purification step, the person skilled in the art must make choices in terms of the resin (base and ligand) and the buffers used. However, there are a great many chromatography resins, based on various bases (agarose, dextran, synthetic polymers, etc.) and various ligands (affinity, cation-exchange, ion-exchange, hydrophobic interactions, etc.), and several buffers may be used for each chromatography resin.

It is thus particularly difficult for the person skilled in the art to select a combination of steps and of specific products capable of significantly reducing the costs of purification of a monoclonal antibody, while maintaining the quality, purity and health safety levels of the purified antibody.

SUMMARY OF THE INVENTION

In the context of the present invention, the inventors demonstrated that a particular combination of purification and viral clearance or inactivation steps makes it possible to reduce by a factor of 3 the costs of purification of a monoclonal antibody, while maintaining the quality, purity and health safety levels of the purified antibody. This substantial decrease in the cost of purification of a monoclonal antibody was enabled by the selection of less expensive products, making it possible to process a larger quantity of antibodies at one time, and by the optimization of the operating conditions of each step so as to maintain the quality, purity and health safety levels of the purified antibody.

In a first aspect, the present invention thus relates to a method for purification of a monoclonal antibody or a fusion protein between the Fc fragment of an antibody and a second polypeptide, comprising:
  a) an affinity chromatography step on a resin having as matrix a cross-linked methacrylate polymer gel, on which protein A is grafted,
  b) a viral inactivation step,
  c) a cation-exchange chromatography step on a resin having as matrix a cross-linked agarose gel, on which sulfonate groups ($-SO_3-$) are grafted via dextran-based spacer arms,
  d) an anion-exchange chromatography step on a hydrophilic polyethersulfone membrane coated with a cross-linked polymer on which quaternary amine groups (Q) are grafted, and
  e) a nanofiltration step with a filter having a dual polyethersulfone membrane having a pore size of about 20 nm.

Advantageously, the cross-linked methacrylate polymer gel on which protein A is grafted used in step a) is in the form of beads having an average diameter of between 30 and 60 µm, advantageously of between 40 and 50 µm. Moreover, the elution buffer used in step a) to elute the antibody is preferably a formate buffer, the latter being advantageously used at a molarity of 5 to 10 mM and at a pH of between 2.6 and 3.6.

Advantageously, step b) is carried out by incubation for 30 to 120 minutes at a temperature of 20 to 25° C. in a medium comprising 0.5 to 2% (v/v) of polyoxyethylene-p-t-octylphenol (CAS no. 9002-93-1).

Advantageously, the buffer used during step d) is a trishydroxymethylaminomethane (TRIS) buffer at a concentration of 15 to 25 mM, a pH of 7.5 to 8.5 and a conductivity of 5 to 15 mS/cm.

Advantageously, step e) further comprises preliminary filtration through a Viresolve Prefilter (VPF, depth filter comprising cellulose fibers, diatomaceous earth and a negatively-charged resin) or Viresolve Pro Shield prefilter (polyethersulfone membrane having a pore size of 0.22 µm functionalized by $SO_3^-$ groups).

Advantageously, the method further comprises an ultrafiltration and/or diafiltration step.

Advantageously, the method according to the invention is implemented on a culture supernatant of a clone producing the monoclonal antibody or the fusion protein between the Fc fragment of an antibody and a second polypeptide.

Advantageously, the method according to the invention is implemented for the purification of a monoclonal antibody, particularly an antibody directed against one of the following antigens: Rhesus D, CD2, CD3, CD4, CD19, CD20, CD22, CD25, CD30, CD33, CD40, CD51 (Integrin alpha-V), CD52, CD80, CTLA-4 (CD152), SLAMF7 (CD319), Her2/neu, EGFR, EPCAM, CCR4, CEA, FR-alpha, GD2, GD3, HLA-DR, IGF1R (CD221), phosphatidylserine, TRAIL-R1, TRAIL-R2, *Clostridium difficile* antigens, *Staphylococcus aureus* antigens (particularly ClfA and lipoteichoic acid), cytomegalovirus antigens (particularly glycoprotein B), *Escherichia coli* antigens (particularly Shiga-like toxin, subunit IIB), respiratory syncytial virus antigens (F protein in particular), hepatitis B virus antigens, influenza A virus antigens (hemagglutinin in particular), *Pseudomonas aeruginosa* serotype IATS O11 antigens, rabies virus antigens (glycoprotein in particular), or phosphatidylserine.

DETAILED DESCRIPTION OF THE INVENTION

Figure 1A:
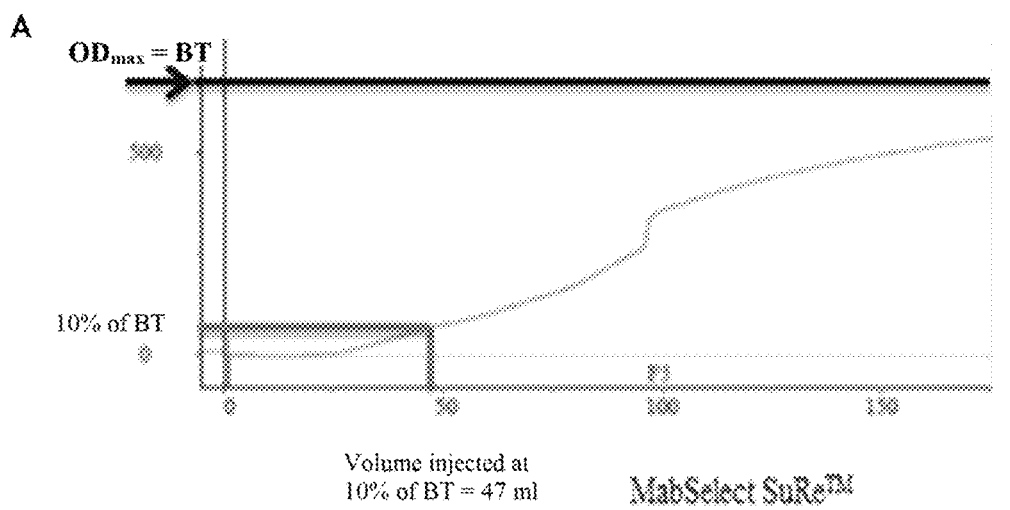
FIG. 1. Determination of the volume injected at the 10% BT point for purification by Protein A affinity chromatography on resins of the type MabSelect SuRe™ (A), Poros GoPure™ (B), Toyopearl AF-rProtein A-650F (C) and Amsphere™ Protein A JWT203 (D).

As indicated above, the methods for purification of monoclonal antibodies impose significant production costs on manufacturers, which it is important to reduce as much as possible in order to lower the cost of monoclonal antibody treatments. However, the existence of numerous separate commercial products that can be used for the purification of monoclonal antibodies and the very great possibility of variations of the operating conditions of each step makes the selection of an appropriate combination of steps, products and operating conditions for reducing the overall cost of purification extremely difficult for the person skilled in the art.

However, the inventors have now demonstrated that a particular combination of purification and viral clearance or inactivation steps makes it possible to reduce the costs of purification of a monoclonal antibody by a factor of 3, while maintaining the quality, purity and health safety levels of the purified antibody. This substantial decrease in the cost of purification of a monoclonal antibody was enabled by the selection of less expensive products, making it possible to process a larger quantity of antibody at one time, and by the optimization of the operating conditions of each step in order to maintain the quality, purity and health safety levels of the purified antibody.

The present invention thus relates to a method for purification of a monoclonal antibody or a fusion protein between the Fc fragment of an antibody and a second polypeptide, comprising:

a) an affinity chromatography step on a resin having as matrix a cross-linked methacrylate polymer gel, on which protein A is grafted, b) a viral inactivation step, c) a cation-exchange chromatography step on a resin having as matrix a cross-linked agarose gel, on which sulfonate groups ($-SO_3-$) are grafted via dextran-based spacer arms, d) an anion-exchange chromatography step on a hydrophilic polyethersulfone membrane coated with a cross-linked polymer on which quaternary amine groups (Q) are grafted, and e) a nanofiltration step with a filter having a dual polyethersulfone membrane having a pore size of about 20 nm.

Starting Material

The method according to the invention is applicable to the purification of both a monoclonal antibody and a fusion protein between the Fc fragment of an antibody and a second polypeptide. Indeed, the first step (step a)) is an affinity chromatography step on a resin bearing protein A, a *Staphylococcus aureus* protein that binds specifically to the Fc fragment of antibodies, and particularly to the human Fc fragment.

Antibody

By "antibody" or "immunoglobulin" is meant a molecule comprising at least one binding domain of a given antigen and a constant domain comprising an Fc fragment capable of binding to Fc receptors (FcR). In most mammals, such as humans and mice, an antibody is composed of 4 polypeptide chains: 2 heavy chains and 2 light chains linked together by a variable number of disulfide bridges that provide the molecule with flexibility. Each light chain consists of a constant domain (CL) and a variable domain (VL); the heavy chains being composed of a variable domain (VH) and 3 or 4 constant domains (CH1 to CH3 or CH1 to CH4) depending on the antibody isotype. In a few rare mammals, such as camels and llamas, antibodies consist of only two heavy chains, each heavy chain comprising a variable domain (VH) and a constant region.

The variable domains are involved in antigen recognition, whereas the constant domains are involved in the biological, pharmacokinetic and effector properties of the antibody. Unlike the variable domains whose sequence varies greatly from one antibody to another, the constant domains are characterized by an amino acid sequence that is very similar from one antibody to another, characteristic of the species and the isotype, with potentially a few somatic mutations. The Fc fragment is naturally composed of the heavy chain constant region with the exception of the CH1 domain, i.e. the lower hinge region and the CH2 and CH3 or CH2 to CH4 constant domains (depending on the isotype). In human IgG1, the complete Fc fragment is composed of the C-terminal part of the heavy chain starting from the cysteine residue at position 226 (C226), the numbering of the amino acid residues in the Fc fragment being throughout the present description that of the Eu index described in Edelman et al. (Edelman, G. M. et al., Proc. Natl. Acad. USA, 63, 78-85 (1969)) and Kabat et al. (Kabat et al., Sequences of Proteins of Immunological Interest, 5th Ed. Public Health Service, National Institutes of Health, Bethesda, Md. (1991)). The Fc fragments corresponding to other types of immunoglobulins can be easily identified by the person skilled in the art by sequence alignments.

The Fcγ fragment is glycosylated at the CH2 domain with the presence, on each of the 2 heavy chains, of an N-glycan linked to the asparagine residue at position 297 (Asn 297). The following binding domains, located in Fcγ, are important for the biochemical properties of the antibody:

FcRn binding domain, involved in the pharmacokinetic properties (in vivo half-life) of the antibody:
Various data suggest that certain residues located at the interface of the CH2 and CH3 domains are involved in FcRn binding.
C1q complement protein binding domain, involved in the complement-dependent cytotoxicity (CDC) response: located in the CH2 domain;
FcR binding domain, involved in phagocytosis or antibody-dependent cell-mediated cytotoxicity (ADCC) type responses: located in the CH2 domain.

Within the meaning of the invention, the Fc fragment of an antibody can be natural, as defined above, or can have been modified in various ways, on the condition of being capable of binding to protein A. The modifications can include the deletion of certain parts of the Fc fragment, provided that the Fc fragment thus obtained is capable of binding to protein A. The modifications can also include various amino acid substitutions capable of affecting the biological properties of the antibody, provided that the Fc fragment thus obtained is capable of binding to protein A. In particular, when the antibody is an IgG, it can comprise mutations intended to increase binding to the receptor FcγRIII (CD16), as described in WO00/42072, Shields et al.-2001, Lazar et al. (Lazar, G. A., et al. Proc Natl Acad Sci USA 103(11): 4005-10), WO2004/029207, WO/2004063351, WO2004/074455. Mutations for increasing binding to FcRn and thus in vivo half-life can also be present, as described for example in Shields et al. (Shields R L, et al. J Biol Chem. 2001 Mar. 2; 276(9):6591-604), Dall'Acqua et al.-2002, Hinton et al.-2004, Dall'Acqua et al.-2006(a), WO00/42072, WO02/060919A2, WO2010/045193, or WO2010/106180A2. Other mutations, such as those for decreasing or increasing binding to complement proteins and thus the CDC response, may or may not be present (see WO99/51642; WO2004074455A2; Idusogie E E et al. J Immunol. 2001; 166:2571-5; Dall'Acqua et al. J Immunol 2006; 177:1129-1138; and Moore G L. et al. mAbs 2:2, 181-189; March/April, 2010).

By "monoclonal antibody" or "monoclonal antibody composition" is meant a composition comprising antibody molecules having an identical and unique antigenic specificity. The antibody molecules present in the composition may vary in terms of their post-translational modifications, and particularly in terms of their glycosylation structures or their isoelectric point, but all have been encoded by the same heavy- and light-chain sequences and thus have, before any post-translational modification, the same protein sequence. Certain differences in protein sequence, related to post-translational modifications (such as for example cleavage of the heavy-chain C-terminal lysine, deamidation of asparagine residues and/or isomerization of aspartate residues), can nevertheless exist between the various antibody molecules present in the composition.

The monoclonal antibody purified in the context of the invention can be advantageously chimeric, humanized or human. Indeed, the *Staphylococcus aureus* protein A has a specific binding affinity for human Fc fragments, and in particular for the human Fcγ fragment.

By "chimeric" antibody is meant an antibody that contains a natural variable region (light chain and heavy chain) derived from an antibody of a given species in combination with the constant regions of the light chain and the heavy chain of an antibody of a species heterologous to said given species. Advantageously, if the monoclonal antibody composition for use as a medicinal product according to the invention comprises a chimeric monoclonal antibody, the latter comprises human constant regions. Starting with a non-human antibody, a chimeric antibody can be prepared using the genetic recombination techniques well-known to the person skilled in the art. For example, the chimeric antibody could be prepared by cloning for the heavy chain and the light chain a recombinant DNA comprising a promoter and a sequence encoding the variable region of the non-human antibody, and a sequence encoding the constant region of a human antibody. For the methods for preparing chimeric antibodies, reference may be made for example to the document Verhoeyen et al. (Verhoeyen et al. BioEssays, 8: 74, 1988).

By "humanized" antibody is meant an antibody that contains CDRs derived from an antibody of non-human origin, the other portions of the antibody molecule being derived from one (or from several) human antibodies. Moreover, certain residues of the framework regions (called FRs) can be modified to retain the binding affinity (Jones et al. Nature, 321: 522-525, 1986; Verhoeyen et al.-1988; Riechmann et al. Nature, 332: 323-327, 1988). The humanized antibodies according to the invention can be prepared by techniques known to the person skilled in the art such as CDR grafting, resurfacing, superhumanization, human string content, FR libraries, guided selection, FR shuffling and humaneering technologies, as summarized in the review by Almagro et al. (Almagro et al. Frontiers in Bioscience 13, 1619-1633, Jan. 1, 2008).

By "human" antibody is meant an antibody the entire sequence of which is of human origin, i.e. the encoding sequences of which have been produced by recombination of human genes encoding the antibodies. Indeed, it is now possible to produce transgenic animals (e.g. mice) which are capable, upon immunization, of producing a complete set of human antibodies in the absence of endogenous production of immunoglobulin (see Jakobovits et al., Proc. Natl. Acad. Sci. USA. 90:2551 (1993); Jakobovits et al., Nature, 362: 255-258 (1993); Bruggermann et al., Year in Immuno., 7:33

(1993); Duchosal et al. Nature 355:258 (1992); U.S. Pat. Nos. 5,591,669; 5,598,369; 5,545,806; 5,545,807; 6,150, 584). Human antibodies can also be obtained from phage display libraries (Hoogenboom et al., J. Mol. Biol., 227:381 (1991); Marks et al., J. Mol. Biol., 222:581-597 (1991); Vaughan et al. Nature Biotech 14:309 (1996)).

The antibodies can be several isotypes, according to the nature of their constant region: the γ, α, μ, ε and δ constant regions correspond respectively to the immunoglobulins IgG, IgA, IgM, IgE and IgD. Advantageously, the monoclonal antibody present in a composition used as a medicinal product in the context of the invention is isotype IgG. Indeed, this isotype shows a capacity to generate antibody-dependent cell-mediated cytotoxicity (ADCC) activity in the greatest number of individuals (human) and is thus chiefly used for pharmaceutical applications of monoclonal antibodies. Moreover, protein A has a specific binding affinity for the human Fcγ fragment.

The γ constant regions comprise several sub-types: γ1, γ2, γ3, these three types of constant regions having the characteristic of binding the human complement, and γ4, thus creating the subisotypes IgG1, IgG2, IgG3 and IgG4. Advantageously, the monoclonal antibody present in a composition used as a medicinal product in the context of the invention is isotype IgG1. Indeed, the Fcγ1 fragment has a particularly high binding affinity for protein A.

The monoclonal antibody composition to be purified by the method according to the invention can be produced by a cell clone, a transgenic non-human animal or a transgenic plant, by technologies well-known to the person skilled in the art.

In particular, cell clones producing the antibody composition to be purified can be obtained by three main technologies:

1) Obtaining a hybridoma by fusion of a B-cell producing the antibody of interest with an immortalized line,
2) Immortalization of a B-cell producing the antibody of interest by the Epstein-Barr virus (EBV),
3) Isolation of sequences encoding an antibody of interest (generally starting with a hybridoma or an immortalized B-cell), cloning into one or more expression vector(s) the sequences encoding the heavy and light chains of the antibody, transformation of a cell line by the expression vector(s), and separation of the various cell clones obtained. An expression vector for the heavy and light chains of the antibody comprises the elements necessary to the expression of the sequences encoding the heavy and light chains of the antibody, and particularly a promoter, a start codon, termination sequences, and suitable transcription regulation sequences. These elements vary according to the host used for the expression and are easily selected by the person skilled in the art in view of his general knowledge. The vector can be particularly a plasmid or viral vector. The transformation techniques are also well-known to the person skilled in the art.

The transformation of cell lines by one or more expression vector(s) of the sequences encoding the heavy and light chains of the antibody is most commonly used, particularly for obtaining chimeric or humanized antibodies.

The transformed cell line is preferably of eukaryotic origin, and can notably be selected from insect, plant, yeast or mammalian cells. The antibody composition can then be produced by culturing the host cell under suitable conditions. Suitable cell lines for the production of antibodies include notably the lines selected from: SP2/0; YB2/0; IR983F; human myeloma Namalwa; PERC6; CHO lines, particularly CHO-K-1, CHO-Lec10, CHO-Lec1, CHO-Lec13, CHO Pro-5, CHO dhfr-, or CHO line deleted for the two alleles encoding the FUT8 gene and/or the GMD gene; Wil-2; Jurkat; Vero; Molt-4; COS-7; 293-HEK; BHK; K6H6; NSO; SP2/0-Ag 14, P3X63Ag8.653, duck embryonic cell line EB66® (Vivalis); and rat hepatoma lines H4-II-e (DSM ACC3129), H4-II-Es (DSM ACC3130) (see WO2012/041768). In a preferred embodiment, the antibody is produced in one of the following lines: YB2/0; CHO line deleted for the two alleles encoding the FUT8 gene and/or the GMD gene; duck embryonic cell line EB66® (Vivalis); and rat hepatoma lines H4-II-e (DSM ACC3129), H4-II-Es (DSM ACC3130). In a preferred embodiment, the antibody is produced in YB2/0 (ATCC CRL-1662).

Alternatively, the antibody composition to be purified can be produced in a transgenic non-human animal.

A transgenic non-human animal can be obtained by direct injection of the gene(s) of interest (here, the rearranged genes encoding the heavy and light chains of the antibody) into a fertilized egg (Gordon et al.-1980). A transgenic non-human animal can also be obtained by introduction of the gene(s) of interest (here, the rearranged genes encoding the heavy and light chains of the antibody) into an embryonic stem cell and preparation of the animal by a chimera aggregation method or a chimera injection method (see Manipulating the Mouse Embryo, A Laboratory Manual, Second edition, Cold Spring Harbor Laboratory Press (1994); Gene Targeting, A Practical Approach, IRL Press at Oxford University Press (1993)). A transgenic non-human animal can also be obtained by a cloning technique in which a nucleus, into which the gene(s) of interest (here, the rearranged genes encoding the heavy and light chains of the antibody) have been introduced, is transplanted into an enucleated egg (Ryan et al., 1997 Science; 278: 873-876; Cibelli et al., 1998 Science, 280: 1256-1258; WO0026357A2). A transgenic non-human animal producing an antibody of interest can be prepared by the methods above.

The antibody can then be accumulated in the transgenic animal and harvested, particularly from the animal's milk or eggs. For producing antibodies in the milk of transgenic non-human animals, preparation methods are notably described in WO9004036A1, WO9517085A1, WO0126455A1, WO2004050847A2, WO2005033281A2, WO2007048077A2. Methods for purifying proteins of interest from milk are also known (see WO0126455A1, WO2007106078A2). The transgenic non-human animals of interest particularly include mice, rabbits, rats, goats, bovines (particularly cows) and poultry (particularly chickens).

The antibody composition to be purified can also be produced in a transgenic plant. Many antibodies have already been produced in transgenic plants and the technologies required for obtaining a transgenic plant expressing an antibody of interest and for recovering the antibody are well-known to the person skilled in the art (see Stoger E, et al. Molecular Breeding 9: 149-158, 2002; Fisher R, et al. Vaccine 21 (2003) 820-825; Ma J K, et al. Nat Rev Genet. 2003 October; 4(10):794-805; Schillberg S, et al. Vaccine 23 (2005) 1764-1769). It is also possible to influence the glycosylation obtained in the plants in order to obtain glycosylation close to that of natural human antibodies (without xylose), but also with low fucosylation, for example using small interfering RNAs (Forthal et al., J Immunol 2010; 185; 6876-6882).

The monoclonal antibody to be purified can be directed against any antigen of interest, and particularly against the following antigens:

Rhesus D, the anti-Rhesus D antibodies being useful for preventing alloimmunization in Rhesus-negative individuals, Antigens expressed by cancer cells, which can be targeted in the treatment of cancers, and particularly: CD20, Her2/neu, CD52, EGFR, EPCAM, CCR4, CTLA-4 (CD152), CD19, CD22, CD3, CD30, CD33, CD4, CD40, CD51 (Integrin alpha-V), CD80, CEA, FR-alpha, GD2, GD3, HLA-DR, IGF1R (CD221), phosphatidylserine, SLAMF7 (CD319), TRAIL-R1, TRAIL-R2.

Antigens expressed by cells infected by pathogenic agents, which can be targeted in the treatment of infections by pathogenic agents, and particularly: *Clostridium difficile* antigens, *Staphylococcus aureus* antigens (particularly ClfA and lipoteichoic acid), cytomegalovirus antigens (particularly glycoprotein B), *Escherichia coli* antigens (particularly Shiga-like toxin, subunit IIB), respiratory syncytial virus antigens (F protein in particular), hepatitis B virus antigens, influenza A virus antigens (hemagglutinin in particular), *Pseudomonas aeruginosa* serotype IATS O11 antigens, rabies virus antigens (glycoprotein in particular), phosphatidylserine.

Antigens expressed by immune cells, which can be targeted for the treatment of autoimmune diseases, and particularly: CD20, CD52, CD25, CD2, CD22, CD3, and CD4.

Fc Fusion Protein

By "fusion protein between the Fc fragment of an antibody and a second polypeptide" or "Fc fusion protein" is meant a protein comprising an Fc fragment of an antibody operably linked to a second polypeptide. Such an Fc fusion protein comprises an Fc fragment conferring thereon the effector and pharmacological properties of an antibody (as well as the capacity to bind to protein A), and a second polypeptide (fusion partner) conferring thereon other biological properties.

Fc fusion proteins comprise, just like monoclonal antibodies, an Fc fragment linked to protein A. Consequently, the technical teachings obtained by the inventors on monoclonal antibodies apply directly to Fc fusion proteins.

The second polypeptide or fusion partner can notably be selected from a receptor (or the binding domain of a receptor to its ligand), a ligand (or the receptor-binding domain of a ligand), an adhesion molecule, a cytokine, a chemokine, or any other protein or protein domain.

Fusion between the Fc fragment and the second polypeptide can be direct or indirect via a linker, which can particularly consist of one or more glycine- or serine-type amino acids.

Such Fc fusion proteins have been developed for various therapeutic applications. Notably, the following Fc fusion proteins can be purified using the method according to the invention:

abatacept and belatacept: fusion proteins between the ectodomain of CTLA-4 and the Fc of IgG1, used in immunosuppression in rheumatoid arthritis (abatacept) and transplantation (belatacept)

etanercept: fusion protein between the ectodomain of the receptor TNF-RII and the Fc of IgG1, used in the treatment of rheumatoid arthritis and psoriasis, alefacept: fusion protein between the ectodomain of LFA-3 (CD58) and the Fc of IgG1, used therapeutically in the treatment of psoriasis, or rilonacept: dimeric fusion protein consisting of the binding domains of the extracellular portions of the interleukin-1 receptor I (IL-1RI) and an IL-1 receptor accessory protein (IL-1RAcP) linked in-line to the Fc portion of human immunoglobulin IgG1, used in the treatment of severe forms of cryopyrin-associated periodic syndromes (CAPS), including familial cold autoinflammatory syndrome (FCAS) and Muckle-Wells syndrome (MWS).

atacicept: recombinant fusion protein that contains the soluble TACI receptor linked to the Fc fragment of a human IgG1, used in the treatment of rheumatoid arthritis, systemic lupus and multiple sclerosis.

briobacept: fusion protein consisting of the BAFF receptor and an IgG1 constant fragment, used in the treatment of rheumatoid arthritis.

Such Fc fusion proteins are produced recombinantly, by any suitable technology particularly selected from those described above for producing recombinant monoclonal antibodies (transformed cell clone, transgenic non-human animal, transgenic plant in particular).

Product to be Purified

The purification method according to the invention is advantageously implemented starting with a composition comprising the antibody in unpurified form, i.e. further comprising other contaminant products (other proteins, DNA, sugars, etc.).

The method according to the invention can thus notably be implemented starting with the following materials:

culture supernatant of a clone producing the monoclonal antibody or the fusion protein between the Fc fragment of an antibody and a second polypeptide, milk from a transgenic non-human animal expressing the monoclonal antibody or the fusion protein between the Fc fragment of an antibody and a second polypeptide, or cell extract from a transgenic plant expressing the monoclonal antibody or the fusion protein between the Fc fragment of an antibody and a second polypeptide.

Many monoclonal antibodies or fusion proteins between the Fc fragment of an antibody and a second polypeptide are produced in transformed cell clones, and the method according to the invention can thus advantageously be implemented on a culture supernatant of a clone producing the monoclonal antibody or the fusion protein between the Fc fragment of an antibody and a second polypeptide. By "clone producing the monoclonal antibody or the fusion protein between the Fc fragment of an antibody and a second polypeptide" is meant a cell (which can notably be selected from those described above) transformed by an expression vector of the monoclonal antibody or the fusion protein between the Fc fragment of an antibody and a second polypeptide. By "culture supernatant" is meant the composition obtained by centrifugation of the culture medium of the producer clone cells and exclusion of the cells or debris present in the culture medium, said culture medium optionally having been first subjected to a lysis step of the producer clone cells.

Step a)

Step a) of the method according to the invention is an affinity chromatography step on a resin having as matrix a cross-linked methacrylate polymer gel, on which protein A is grafted. This step makes it possible to purify in a very substantial manner the antibody or the Fc fusion protein, due to the high affinity and the high specificity of protein A for the Fc fragment of antibodies.

Protein A

Affinity chromatography makes it possible to specifically separate the molecules bound to a particular ligand. In the context of antibody purification, a protein A affinity chromatography step is commonly used, this protein specifically binding to the Fc fragment of antibodies, particularly to the human Fc fragment, and more particularly to the Fcγ fragment and in particular human Fcγ1.

By "protein A" is meant the *Staphylococcus aureus* protein encoded by the spa gene, or a derivative or a fragment of this protein capable of binding to the Fc fragment of a monoclonal antibody. The *Staphylococcus aureus* protein A encoded by the spa gene is a *Staphylococcus aureus* membrane protein comprising 5 homologous N-terminal domains (E-D-A-B-C) each capable of binding to the Fc fragment of antibodies, the C-terminal region (X) serving to anchor the protein in the bacterial membrane. A native protein A can be isolated directly from *Staphylococcus aureus* cultures secreting protein A, or from recombinant *Escherichia coli* (*E. coli*) bacterial cultures expressing protein A (Löfdahl et al. Proc Natl Acad Sci USA. 1983 February; 80(3):697-701; Uhlén et al. J Biol Chem. 1984 Feb. 10; 259(3):1695-702). In order to optimize its use for affinity chromatography, various fragments or variants of protein A capable of binding specifically and with high affinity to the Fc fragment of antibodies have been proposed. In particular, various native or derived protein A domains and/or fragments of these domains have been proposed in repeating form (dimers, tetramers or hexamers in particular) for purifying antibodies. For example, a "Z" fragment of the B domain of protein A has been proposed for use in antibody purification (U.S. Pat. No. 6,013,763). Different variants of recombinant protein A or of a recombinant protein A fragment comprising an N-terminal cysteine residue or arginine residue allowing easier attachment the chromatography matrix have also been disclosed (U.S. Pat. Nos. 5,084,559; 5,260,373; 6,399,750). Variants of protein A or of functional protein A fragments having improved stability in alkaline conditions have also been disclosed (U.S. Pat. No. 7,709,209; WO2012/083425), these variants being used to allow repeated sanitization of protein A affinity chromatography columns without too great of a release of protein A.

Affinity Chromatography Matrix

In the method according to the invention, protein A is attached to an affinity chromatography matrix consisting of a cross-linked methacrylate polymer gel.

By "cross-linked methacrylate polymer" is meant any cross-linked polymer or copolymer comprising methacrylate monomers. By "methacrylate" is meant the methacrylate ion of formula ($CH_2$=$C(CH_3)COO^-$), as well as the salts and the esters of this ion.

Indeed, the inventors demonstrated that this particular type of resin makes it possible to increase the antibody load purified at one time, to guarantee a good yield (at least 90%) and to obtain an eluate with a clear appearance (see Example 1).

The cross-linked methacrylate polymer gel on which protein A is grafted used in step a) can appear advantageously in the form of beads having an average diameter of between 30 and 60 μm, advantageously of between 40 and 50 μm, and particularly of about 45, 49 or 50 μm.

Depending on the protein A used, it can be attached to the affinity chromatography matrix by various common types of coupling, such as CNBr multipoint coupling (coupling between the primary amino functions of protein A and a CNBr-activated matrix), single-point coupling by a thioether bond between the matrix and a cysteine residue of protein A, obtained notably by activation of the matrix by an epoxide or an epichlorohydrin. Examples of matrices consisting of a cross-linked methacrylate polymer gel in the form of beads having an average diameter of between 40 and 50 μm, on which protein A is grafted, include the following matrices: TOYOPEARL® AF-rProtein A HC-650F (hydroxylated methacrylate polymer matrix in the form of beads having an average diameter of 45 μm, on which recombinant protein A is grafted, marketed by TOSOH BIOSCIENCE), Amsphere™ Protein A JWT203 (methacrylate polymer resin in the form of beads having an average diameter of 49 μm, on which is grafted a modified alkaline-stable C domain tetramer produced in *E. coli*, marketed by JSR Corporation), Amsphere™ Protein A A3 (methacrylate/hydrophilic monomer copolymer resin in the form of beads having an average diameter of between 20 and 80 μm, preferably between 30 and 70 μm, between 40 and 60 μm, or between 40 and 50 μm, on which is grafted a modified alkaline-stable C domain tetramer produced in *E. coli*, marketed by JSR Corporation). Advantageously, the resin having as matrix a cross-linked methacrylate polymer gel, on which protein A is grafted, is selected from:

a hydroxylated methacrylate polymer matrix in the form of beads having an average diameter of 45 μm, on which recombinant protein A is grafted (particularly the resin TOYOPEARL® AF-rProtein A HC-650F);

a methacrylate polymer resin in the form of beads having an average diameter of 49 μm, on which is grafted a modified alkaline-stable C domain tetramer produced in *E. coli* (particularly the resin Amsphere™ Protein A JWT203), and a methacrylate/hydrophilic monomer copolymer resin in the form of beads having an average diameter of between 20 and 80 μm, preferably between 30 and 70 μm, between 40 and 60 μm, or between 40 and 50 μm, on which is grafted a modified alkaline-stable C domain tetramer produced in *E. coli* (particularly the resin Amsphere™ Protein A A3).

More advantageously, the resin is:

a methacrylate polymer resin in the form of beads having an average diameter of 49 μm, on which is grafted a modified alkaline-stable C domain tetramer produced in *E. coli* (particularly the resin Amsphere™ Protein A JWT203), or methacrylate/hydrophilic monomer copolymer resin in the form of beads having an average diameter of between 20 and 80 μm, preferably between 30 and 70 μm, between 40 and 60 μm, or between 40 and 50 μm, on which is grafted a modified alkaline-stable C domain tetramer produced in *E. coli* (particularly the resin Amsphere™ Protein A A3).

More advantageously, the resin is a methacrylate/hydrophilic monomer copolymer resin in the form of beads having an average diameter of between 20 and 80 μm, preferably between 30 and 70 μm, between 40 and 60 μm, or between 40 and 50 μm, on which is grafted a modified alkaline-stable C domain tetramer produced in *E. coli* (particularly the resin Amsphere™ Protein A A3). Indeed, such a resin has a high load capacity and makes it possible to obtain eluates with a good yield, a low turbidity, and a good removal of impurities, particularly host cell proteins (HCP) and host cell DNA (HC-DNA) (see Example 4).

Wash (Optional)

Step a) of the method according to the invention can further comprise, in an optional but preferred manner, a sub-step of washing the resin having as matrix a cross-linked methacrylate polymer gel, on which protein A is grafted, on which the monoclonal antibody or the fusion protein between the Fc fragment of an antibody and a second polypeptide was bound.

Such a washing makes it possible notably to improve the removal of impurities, particularly host cell proteins (HCP) and host cell DNA (HC-DNA).

This washing is advantageously carried out using a saline solution comprising an NaCl concentration of at least 1M, advantageously at least 1.2M, at least 1.3M, at least 1.4M, at least 1.5M, at least 1.6M, indeed at least 1.7M. Advantageously, the NaCl concentration of the saline solution used for washing is between 1M and 2.5M, between 1M and 2.1M, between 1M and 2M, between 1M and 1.9M, between 1M and 1.8M, between 1M and 1.7M, between 1.1M and 2.5M, between 1.1M and 2.1M, between 1.1M and 2M, between 1.1M and 1.9M, between 1.1M and 1.8M, between 1.1M and 1.7M, between 1.2M and 2.5M, between 1.2M and 2.1M, between 1.2M and 2M, between 1.2M and 1.9M, between 1.2M and 1.8M, between 1.2M and 1.7M, between 1.3M and 2.5M, between 1.3M and 2M, between 1.3M and 1.9M, between 1.3M and 1.8M, between 1.3M and 1.7M, between 1.4M and 2.5M, between 1.4M and 2M, between 1.4M and 1.9M, between 1.4M and 1.8M, between 1.4M and 1.7M, between 1.5M and 2.5M, between 1.5M and 2M, between 1.5M and 1.9M, between 1.5M and 1.8M, between 1.5M and 1.7M, between 1.6M and 2.5M, between 1.6M and 2M, between 1.6M and 1.9M, between 1.6M and 1.8M, between 1.6M and 1.7M, between 1.7M and 2.5M, between 1.7M and 2M, between 1.7M and 1.9M, between 1.7M and 1.8M, and particularly about 1.7M. A solution having the following composition can be used in particular: Tris buffer (25 mM), EDTA (5 mM), pH 7.1, and NaCl within one of the concentration ranges described above. Although said wash can be used for any affinity chromatography matrix consisting of a cross-linked methacrylate polymer gel, it is particularly advantageous when the affinity chromatography matrix is a methacrylate/hydrophilic monomer copolymer resin in the form of beads having an average diameter of between 20 and 80 μm, preferably between 30 and 70 μm, between 40 and 60 μm, or between 40 and 50 μm, on which is grafted a modified alkaline-stable C domain tetramer produced in *E. coli*, such as the resin Amsphere™ Protein A A3 marketed by JSR Corporation.

Elution Buffer

During step a), the monoclonal antibody composition or the Fc fusion protein composition to be purified is injected onto a resin having as matrix a cross-linked methacrylate polymer gel, on which protein A is grafted, equilibrated with a neutral pH buffer, to which the monoclonal antibody or the Fc fusion protein will bind via the Fc fragment.

The resin is then washed to remove the contaminants not bound to the resin, then the monoclonal antibody or the Fc fusion protein is eluted using a buffer that breaks the bond between the protein A and the Fc fragment of the antibody or of the Fc fusion protein.

Various types of buffers can be used for the elution. In particular, the elution can be obtained at acidic pH, and buffers using various weak acids can thus be used for the elution.

However, in the context of the present invention, the inventors demonstrated that it was particularly advantageous to use a sodium formate buffer. Advantageously, the sodium formate buffer is used at a molarity of 5 to 10 mM, advantageously 5 to 9 mM, 5 to 8 mM, 5 to 7 mM, 5 to 6 mM, 6 to 10 mM, 6 to 9 mM, 6 to 8 mM, 6 to 7 mM, 7 to 10 mM, 7 to 9 mM, 7 to 8 mM, 8 to 10 mM, 8 to 9 mM, or 9 to 10 mM, more advantageously 5 to 9 mM, 5 to 8 mM, 5 to 7 mM, 5 to 6 mM and particularly about 5 mM. Advantageously, the sodium formate buffer is used at a pH of between 2.6 and 4, advantageously between 2.7 and 4, between 2.8 and 4, between 2.9 and 4, between 3.0 and 4, between 3.1 and 4, between 3.2 and 4, between 3.3 and 4, between 3.4 and 4, between 3.5 and 4, between 3.6 and 4, between 3.7 and 4, between 3.8 and 4, between 3.9 and 4, between 2.6 and 3.9, between 2.7 and 3.9, between 2.8 and 3.9, between 2.9 and 3.9, between 3.0 and 3.9, between 3.1 and 3.9, between 3.2 and 3.9, between 3.3 and 3.9, between 3.4 and 3.9, between 3.5 and 3.9, between 3.6 and 3.9, between 3.7 and 3.9, between 3.8 and 3.9, between 2.6 and 3.8, between 2.7 and 3.8, between 2.8 and 3.8, between 2.9 and 3.8, between 3.0 and 3.8, between 3.1 and 3.8, between 3.2 and 3.8, between 3.3 and 3.8, between 3.4 and 3.8, between 3.5 and 3.8, between 3.6 and 3.8, between 3.7 and 3.8, between 2.6 and 3.7, between 2.7 and 3.7, between 2.8 and 3.7, between 2.9 and 3.7, between 3.0 and 3.7, between 3.1 and 3.7, between 3.2 and 3.7, between 3.3 and 3.7, between 3.4 and 3.7, between 3.5 and 3.7, between 3.6 and 3.7, between 2.6 and 3.6, between 2.7 and 3.6, between 2.8 and 3.6, between 2.9 and 3.6, between 3.0 and 3.6, between 3.1 and 3.6, between 3.2 and 3.6, between 3.3 and 3.6, between 3.4 and 3.6, between 3.5 and 3.6, between 2.6 and 3.5, between 2.7 and 3.5, between 2.8 and 3.5, between 2.9 and 3.5, between 3.0 and 3.5, between 3.1 and 3.5, between 3.2 and 3.5, between 3.3 and 3.5, between 3.4 and 3.5, between 2.6 and 3.4, between 2.7 and 3.4, between 2.8 and 3.4, between 2.9 and 3.4, between 3.0 and 3.4, between 3.1 and 3.4, between 3.2 and 3.4, between 3.3 and 3.4, between 2.6 and 3.3, between 2.7 and 3.3, between 2.8 and 3.3, between 2.9 and 3.3, between 3.0 and 3.3, between 3.1 and 3.3, between 3.2 and 3.3, between 2.6 and 3.2, between 2.7 and 3.2, between 2.8 and 3.2, between 2.9 and 3.2, between 3.0 and 3.2, between 3.1 and 3.2, between 2.6 and 3.1, between 2.7 and 3.1, between 2.8 and 3.1, between 2.9 and 3.1, between 3.0 and 3.1, between 2.6 and 3.0, between 2.7 and 3.0, between 2.8 and 3.0, between 2.9 and 3.0, between 2.6 and 2.9, between 2.7 and 2.9, between 2.8 and 2.9, between 2.6 and 2.8, between 2.7 and 2.8, or between 2.6 and 2.7, more advantageously between 2.7 and 3.5, between 2.8 and 3.4, between 2.9 and 3.3, between 3.0 and 3.2, indeed about 3.1, or between 3.6 and 4, or between 3.1 and 3.6.

When the affinity chromatography matrix is a methacrylate polymer resin in the form of beads having an average diameter of 49 μm, on which is grafted a modified alkaline-stable C domain tetramer produced in *E. coli*, such as the resin Amsphere™ Protein A JWT203 marketed by JSR Corporation, the optimal elution pH was determined to be about 3.1, and any elution pH range mentioned above bracketing this optimal value is preferred.

When the affinity chromatography matrix is a methacrylate/hydrophilic monomer copolymer resin in the form of beads having an average diameter of between 20 and 80 μm, preferably between 30 and 70 μm, between 40 and 60 μm, or between 40 and 50 μm, on which is grafted a modified alkaline-stable C domain tetramer produced in *E. coli*, such as the resin Amsphere™ Protein A A3 marketed by JSR Corporation, the optimal elution pH was determined to be about 3.6, and any elution pH range mentioned above bracketing this optimal value is preferred.

Advantageously, sodium formate buffer is used:
at a molarity of 5 to 10 mM, advantageously 5 to 9 mM, 5 to 8 mM, 5 to 7 mM, 5 to 6 mM, 6 to 10 mM, 6 to 9 mM, 6 to 8 mM, 6 to 7 mM, 7 to 10 mM, 7 to 9 mM, 7 to 8 mM, 8 to 10 mM, 8 to 9 mM, or 9 to 10 mM, more advantageously 5 to 9 mM, 5 to 8 mM, 5 to 7 mM, 5 to 6 mM and particularly of about 5 mM, and at a pH of between 2.6 and 4, advantageously between 2.7 and 4, between 2.8 and 4, between 2.9 and 4, between 3.0 and 4, between 3.1 and 4, between 3.2 and 4, between 3.3 and 4, between 3.4 and 4, between 3.5 and 4, between 3.6 and 4, between 3.7 and 4, between 3.8 and 4, between 3.9 and 4, between 2.6 and 3.9, between 2.7 and 3.9, between 2.8 and 3.9, between 2.9 and 3.9, between 3.0 and 3.9, between 3.1 and 3.9, between 3.2 and 3.9, between 3.3 and 3.9, between 3.4 and 3.9, between 3.5 and 3.9, between 3.6 and 3.9, between 3.7 and 3.9, between 3.8 and 3.9, between 2.6 and 3.8, between 2.7 and 3.8, between 2.8 and 3.8, between 2.9 and 3.8, between 3.0 and 3.8, between 3.1 and 3.8, between 3.2 and 3.8, between 3.3 and 3.8, between 3.4 and 3.8, between 3.5 and 3.8, between 3.6 and 3.8, between 3.7 and 3.8, between 2.6 and 3.7, between 2.7 and 3.7, between 2.8 and 3.7, between 2.9 and 3.7, between 3.0 and 3.7, between 3.1 and 3.7, between 3.2 and 3.7, between 3.3 and 3.7, between 3.4 and 3.7, between 3.5 and 3.7, between 3.6 and 3.7, between 2.6 and 3.6, between 2.7 and 3.6, between 2.8 and 3.6, between 2.9 and 3.6, between 3.0 and 3.6, between 3.1 and 3.6, between 3.2 and 3.6, between 3.3 and 3.6, between 3.4 and 3.6, between 3.5 and 3.6, between 2.6 and 3.5, between 2.7 and 3.5, between 2.8 and 3.5, between 2.9 and 3.5, between 3.0 and 3.5, between 3.1 and 3.5, between 3.2 and 3.5, between 3.3 and 3.5, between 3.4 and 3.5, between 2.6 and 3.4, between 2.7 and 3.4, between 2.8 and 3.4, between 2.9 and 3.4, between 3.0 and 3.4, between 3.1 and 3.4, between 3.2 and 3.4, between 3.3 and 3.4, between 2.6 and 3.3, between 2.7 and 3.3, between 2.8 and 3.3, between 2.9 and 3.3, between 3.0 and 3.3, between 3.1 and 3.3, between 3.2 and 3.3, between 2.6 and 3.2, between 2.7 and 3.2, between 2.8 and 3.2, between 2.9 and 3.2, between 3.0 and 3.2, between 3.1 and 3.2, between 2.6 and 3.1, between 2.7 and 3.1, between 2.8 and 3.1, between 2.9 and 3.1, between 3.0 and 3.1, between 2.6 and 3.0, between 2.7 and 3.0, between 2.8 and 3.0, between 2.9 and 3.0, between 2.6 and 2.9, between 2.7 and 2.9, between 2.8 and 2.9, between 2.6 and 2.8, between 2.7 and 2.8, or between 2.6 and 2.7, more advantageously between 2.7 and 3.5, between 2.8 and 3.4, between 2.9 and 3.3, between 3.0 and 3.2, indeed about 3.1, or between 3.6 and 4, or between 3.1 and 3.6.

Indeed, this type of buffer makes it possible to obtain a satisfactory yield, a clear or slightly opalescent eluate and a satisfactory volume, as well as a very small proportion of antibody aggregates. That is not the case for buffers such as sodium acetate dihydrate or trisodium citrate dihydrate, which lead to moderately or highly opalescent eluates, or maleic acid, 0.5M NaOH buffer which leads to a significant formation of antibody aggregates (see Example 1).

Moreover, this type of buffer allows a good removal of impurities, particularly host cell proteins (HCP) and host cell DNA (HC-DNA) (see Example 4).

At the conclusion of the elution of the antibody or the Fc fusion protein, the eluate can be neutralized, i.e. brought to a pH of between 5 and 7, particularly of between 5.5 and 6.5, and particularly of about 6.0. This neutralization can notably be carried out by adding a suitable quantity of 1M Tris buffer (pH 7.5) or 1M sodium hydroxide (NaOH).

Thus, the specific choices made by the inventors concerning the affinity chromatography matrix and the elution buffer make it possible to significantly reduce the cost of this step (increased load, very good yield, relatively inexpensive matrix), while guaranteeing a high purification and a good quality of the purified antibody (clear or slightly opalescent eluate, very small proportion of aggregates).

Step b)

Step b) of the method according to the invention is a viral inactivation step.

By "viral inactivation step" is meant a step in which viruses are not removed from the solution (antigens can still be detected), but are rendered inactive and thus harmless. These steps include in particular dry heating, pasteurization, and treatment with solvent-detergent or with a detergent alone. These various viral inactivation steps are well-known to the person skilled in the art (see in particular the WHO guidelines concerning viral inactivation and removal procedures for ensuring the viral safety of products derived from human blood plasma, available on the WHO website).

Advantageously, in the method according to the invention, the viral inactivation step is a step of solvent-detergent treatment or treatment with a detergent alone. A solvent-detergent treatment is carried out by treating the solution with a mixture of solvent, particularly tri-(N-butyl)-phosphate (TnBP), and of a detergent, particularly Polysorbate 80 (Polyoxyethylene (20) sorbitan monooleate) or polyoxyethylene-p-t-octylphenol (CAS no. 9002-93-1), under suitable conditions. An exemplary solvent-detergent treatment step is carried out in the presence of 1% (weight/volume) of Polysorbate 80 and 0.3% (volume/volume) of TnBP for at least 7 hours at 25±1° C. The viral inactivation step can also be carried out by treatment with a detergent alone, such as Polysorbate 80 (Polyoxyethylene (20) sorbitan monooleate) or polyoxyethylene-p-t-octylphenol (CAS no. 9002-93-1). An example of such a treatment is an incubation for 30 to 120 minutes (particularly for about 1 hour) at a temperature of 20 to 25° C. (particularly at a temperature of about 21 or 22° C.) in a medium comprising 0.5 to 2% (v/v) (particularly about 1% v/v) of polyoxyethylene-p-t-octylphenol (CAS no. 9002-93-1).

Step c)

Step c) is directed at improving the purification of the monoclonal antibody or the Fc fusion protein by removing various contaminants, such as host cell proteins or residual nucleic acids, protein A that may have been released during step a), or solvent and/or detergent that may have been used in step b).

Step c) of the method according to the invention is a cation-exchange chromatography step on a resin having as matrix a cross-linked agarose gel, on which sulfonate groups (—SO$_3$—) are grafted via dextran-based spacer arms.

Indeed, the inventors demonstrated that the use of such a resin makes it possible to increase the load of monoclonal antibody or of Fc fusion protein that can be processed at one time, thus reducing purification costs (see Example 2).

In this step, the monoclonal antibody composition or the Fc fusion protein composition derived from the viral inactivation step b) is applied to a resin having as matrix a cross-linked agarose gel, on which sulfonate groups (—SO$_3$—) are grafted via dextran-based spacer arms.

The conductivity and/or the pH of the composition derived from the viral inactivation step b) can be advantageously adjusted before application on the resin. In particular, the conductivity can be adjusted to a value of between 3 and 7 mS/cm, particularly of between 4 and 6 mS/cm and particularly of about 5 mS/cm. The conductivity adjustment can notably be carried out by adding a suitable quantity of purified water, of a sodium acetate buffer or advantageously of a formate buffer. The pH, in turn, can be adjusted to a value of between 5 and 7, particularly of between 5.5 and 6.5, and particularly of about 6.0. The pH adjustment can notably be carried out by adding a suitable quantity of 0.5M sodium hydroxide (NaOH).

The cross-linked agarose gel, on which sulfonate groups (—$SO_3$—) are grafted via dextran-based spacer arms, used in step c) can appear advantageously in the form of beads having an average diameter of between 10 and 200 μm, advantageously of between 50 and 150 μm, and particularly of about 90 μm.

Examples of matrices consisting of a cross-linked agarose gel, on which sulfonate groups (—$SO_3$—) are grafted via spacer arms, include the following matrices: Capto™ S (cross-linked agarose gel matrix, on which sulfonate groups (—$SO_3$—) are grafted via dextran-based spacer arms, in the form of beads having an average diameter of 90 μm, marketed by GE Healthcare Life Sciences), Fractogel® EMD $SO_3^-$ (methacrylate polymer matrix, on which sulfonate groups (—$SO_3$—) are grafted via long chains of linear acrylamide polymer comprising 15 to 50 acrylamide units, in the form of beads having an average diameter of 30 (type S) or 65 μm (type M)), and Eshmuno®S (hydrophilic cross-linked polyvinylether matrix, on which sulfonate groups (—$SO_3$—) are grafted via spacer arms, in the form of beads having an average diameter of 75-95 μm). Advantageously, the resin having as matrix a cross-linked agarose gel, on which are grafted is selected from a cross-linked agarose gel matrix, on which sulfonate groups (—$SO_3$—) are grafted via dextran-based spacer arms, in the form of beads having an average diameter of 90 μm (Capto'S resin in particular), a methacrylate polymer matrix, on which sulfonate groups (—$SO_3$—) are grafted via long chains of linear acrylamide polymer comprising 15 to 50 acrylamide units, in the form of beads having an average diameter of 30 (type S) or 65 μm (type M) (Fractogel® EMD $SO_3^-$ resin in particular) and a hydrophilic cross-linked polyvinylether matrix, on which sulfonate groups (—$SO_3$—) are grafted via spacer arms, in the form of beads having an average diameter of 75-95 μm (Eshmuno®S resin in particular), more advantageously the resin is a cross-linked agarose gel matrix, on which sulfonate groups (—$SO_3$—) are grafted via dextran-based spacer arms, in the form of beads having an average diameter of 90 μm (Capto™ S resin in particular).

The elution can notably be carried out by increasing the conductivity and/or the pH. In particular, the elution buffer can have a conductivity of between 16 to 20 mS/cm, particularly of between 17 and 19 mS/cm and particularly of about 18 mS/cm. The elution buffer can have a pH of between 6 and 8, particularly of between 6.5 and 7.5, and particularly of about 7.0. It can notably be a 20 mM Tris, QS NaCl buffer (conductivity 18 mS/cm, pH 7.0).

The flow rate of the chromatography step is advantageously adjusted to a value corresponding to a residence time of between 1 and 3 minutes, advantageously of between 1.5 and 2.5 minutes and particularly of about 2 minutes. As a function of the volume of gel, the suitable flow rate can be calculated using the following formula:

flow rate (mL/min)=volume of gel (mL)/residence time (min).

Step d)

Step d) of the method according to the invention is directed at further improving the purification of the monoclonal antibody or the Fc fusion protein by removing various contaminants, such as host cell proteins or residual nucleic acids, protein A that may have been released during step a), or solvent and/or detergent that may have been used in step b). It is particularly effective for removing residual nucleic acids.

It is an anion-exchange chromatography step on a hydrophilic polyethersulfone membrane coated with a cross-linked polymer on which quaternary amine groups (Q) are grafted.

The membrane has advantageously an average pore size of between 0.5 and 1 μm, advantageously of between 0.6 and 0.9 μm, of between 0.7 and 0.9 μm, and particularly of about 0.8 μm.

The membrane advantageously comprises several layers of polyethersulfone coated with a cross-linked polymer on which quaternary amine groups (Q) are grafted, advantageously between 10 and 20 layers, notably between 14 and 18 layers, and in particular 16 layers.

An example of such a membrane is the Mustang® Q membrane (hydrophilic membrane having 16 layers of polyethersulfone having an average pore size of 0.8 μm, coated with a cross-linked polymer on which quaternary amine groups (Q) are grafted) marketed by Pall.

In this step d), the monoclonal antibody composition or the Fc fusion protein composition derived from the cation-exchange chromatography step c) is applied to a hydrophilic polyethersulfone membrane coated with a cross-linked polymer on which quaternary amine groups (Q) are grafted.

The conductivity and/or the pH of the composition derived from the cation-exchange chromatography step c) can be advantageously adjusted before application on the membrane. In particular, the conductivity can be adjusted to a value of between 8 and 12 mS/cm, notably of between 9 and 11 mS/cm and particularly of about 10 mS/cm. The conductivity adjustment can notably be carried out by adding a suitable quantity of 20 mM phosphate buffer or advantageously 20 mM Tris buffer. The pH, in turn, can be adjusted to a value of between 6 and 10, notably between 7.0 and 9.0, between 7.5 and 8.5, and particularly of about 8.0. The pH adjustment can notably be carried out by adding a suitable quantity of 0.5M sodium hydroxide (NaOH).

The membrane is advantageously equilibrated with a Tris buffer, particularly a Tris buffer having the following characteristics:

a concentration of between 15 and 25 mM, between 16 and 24 mM, between 17 and 23 mM, between 18 and 22 mM, between 19 and 21 mM, particularly of about 20 mM, a pH of between 6 and 10, between 7.0 and 9.0, between 7.5 and 8.5, particularly of about 8.0, a conductivity of between 8 and 12 mS/cm, notably between 9 and 11 mS/cm and particularly of about 10 mS/cm.

Step e)

Step d) of the method according to the invention is directed at removing the viruses, and in particular the small non-enveloped viruses that are more resistant to viral inactivation treatments, which may be found in the purified antibody composition or the purified Fc fusion protein composition, in order to guarantee the viral safety of the final pharmaceutical product.

Indeed, the traditional viral inactivation techniques, and in particular solvent-detergent treatment or treatment with detergent alone, have a limited effectiveness with regard to non-enveloped viruses, such as the parvoviruses or the hepatitis A virus.

However, nanofiltration, which is based on a particle-size exclusion mechanism, is known to be effective on non-enveloped viruses. The most commonly used filters for excluding small non-enveloped viruses are the Planova® filters marketed by Asahi Kasei, particularly the Planova® 15N and Planova® 20N filters, having respectively an average pore size of 15 and 19 nm. These filters, consisting of a hollow fiber membrane made of cuprammonium-regenerated cellulose, are characterized by a narrow pore size distribution (±2 nm around the average size). However, these filters are very expensive and do not allow the processing of a large protein load in a limited amount of time (e.g., acceptable processing time of 4 hours), without substantially increasing the filtration surface area (and thus, ultimately, the cost of this step).

In the context of the present invention, the inventors demonstrated that it is highly advantageous to use a Viresolve® Pro filter (filter having a dual asymmetrical polyethersulfone membrane retaining at least 4 log of viruses having a size of at least 20 nm) rather than a Planova® 15N or Planova® 20N filter, the Viresolve® Pro filter making it possible to nanofilter a much larger antibody load than the Planova® 15N and Planova® 20N filters (see Example 4).

Step e) thus consists of a nanofiltration step with a filter having a dual polyethersulfone membrane having a pore size of about 20 nm.

Such filters notably include the Viresolve® Pro filter (filter having a dual asymmetrical polyethersulfone membrane having a pore size of about 20 nm, marketed by Merck-Millipore) and the Virosart® CPV filter (filter having a dual symmetrical polyethersulfone membrane having a pore size of about 20 nm, marketed by Sartorius).

The nanofiltration of step e) is advantageously carried out using a filter having a dual asymmetrical polyethersulfone membrane having a pore size of about 20 nm, such as the Viresolve® Pro filter marketed by Merck-Millipore. By "a pore size of about 20 nm" is meant that the average pore size of the filter is between 17 and 25 nm, advantageously between 17 and 24 nm, between 17 and 23 nm, between 17 and 22 nm, between 17 and 21 nm, between 17 and 20 nm, between 18 and 25 nm, between 18 and 24 nm, between 18 and 23 nm, between 18 and 22 nm, between 18 and 21 nm, between 18 and 20 nm, between 19 and 25 nm, between 19 and 24 nm, between 19 and 23 nm, between 19 and 22 nm, between 19 and 21 nm, between 19 and 20 nm, between 20 and 25 nm, between 20 and 24 nm, between 20 and 23 nm, between 20 and 22 nm, or between 20 and 21 nm.

In an advantageous embodiment, step e) further comprises a preliminary filtration step through a depth filter comprising cellulose fibers, diatomaceous earth and a negatively-charged resin (Viresolve Prefilter, or VPF) or a polyethersulfone membrane having a pore size of 0.22 μm functionalized by $SO_3^-$ groups (Viresolve Pro Shield prefilter in particular).

Optional Steps

The method according to the invention can further comprise an ultrafiltration and/or diafiltration step, which can take place either between the anion-exchange chromatography step d) and the nanofiltration step e) or after the nanofiltration step e). Such a step can notably be carried out using cassettes of the type Centramate 50 kDa (marketed by Pall) or Pellicon 2 (marketed by Merck Millipore) with a dialysis buffer comprising polysorbate 80 when the ultrafiltration takes place after the nanofiltration step e).

Moreover, one or more sterilizing filtration steps through filters having a pore size of about 0.1 to 0.5 μm (notably of about 0.2 μm) can be present at various stages of the method according to the invention. These steps can notably be carried out using a 0.22 μm Millipak filter.

The following examples are directed at illustrating the present invention.

EXAMPLES

Example 1: Optimization of the Protein A Affinity Chromatography Step a)

The protein A affinity chromatography step is an essential step in antibody purification, but it is also the most expensive step of antibody purification methods.

In order to significantly reduce the cost of this step, while maintaining the purity and the quality of the product, the inventors tested various protein A affinity chromatography resins and various elution buffers, and measured the influence of the resin and the elution buffer on a certain number of parameters.

Materials and Methods

Comparison of Four Protein A Affinity Chromatography Resins

Columns Tested and Preparation

The characteristics of the columns tested are:

TABLE 1

Characteristics of the columns tested

| Column | Lot | Volume (mL) | Dimensions (cm) | Resin | Average bead size |
|---|---|---|---|---|---|
| MabSelect SuRe ™ | 10111269 | 4.7 | 4.7 × 0.77 | highly cross-linked agarose | 85 μm |
| Poros GoPure ™ | 121004 | 5.655 | 1.2 × 5 | cross-linked poly(styrene-divinylbenzene) coated with cross-linked polyhydroxylated polymer | 45 μm |
| Toyopearl AF-rProtein A-650F | 0022810 | 5.02 | 14.6 × 3 | methacrylic polymer | 45 μm |
| Amsphere Protein A JWT203 | 10000006-C03 | 5 | 11.3 × 5 | methacrylic polymer | 49 μm |

The columns are sanitized according to the following sequence:

TABLE 2

Column sanitization sequence

| Solution | Column volume (CV) | Flow rate (mL/min) |
|---|---|---|
| Purified water | 2 | 3 |
| 0.5M NaOH | 5 | 3 then 30 min of contact time |
| Purified water | QS pH < 8.0 | 3 |
| 2M NaCl | 5 | 3 |

Determination of the "Breakthrough" Point

A 2.3 g/L solution of thawed, 0.2 μm-filtered antibody is injected into the chromatography apparatus (Akta Basic) without passing through the column. The OD at 280 nm thus read corresponds to the maximum OD at 280 nm. The latter is 664 mAU. The point corresponding to a 10% loss of load from the column, called "breakthrough" (10% BT), is thus determined at 66.4 mAU. The UV cell and the apparatus circuit are then rinsed with water then with equilibration buffer.

Determination of dynamic binding capacity at 10% passage ($DBC_{10\% \, BT}$)

Once connected, the column is equilibrated with Buffer A (25 mM Tris, 25 mM NaCl, 5 mM EDTA, pH 7.1). When the column is equilibrated, a pump wash step is carried out with the antibody solution to fill the tubing upstream of the column. Irrespective of the column, the thawed, 0.2 μm-filtered antibody solution is injected at a flow rate of 3 mL/min (i.e. a residence time of about 1.6 min) and the OD at 280 nm is monitored.

Comparison of Four Elution Buffers

Four protein A affinity chromatography elution buffers were tested at various concentrations and pH values, and their impact on the appearance of the eluate and the percentage of monomeric IgG (and thus on the presence of aggregates) was analyzed.

Composition of the Buffers Tested
The four buffers tested are the following:

TABLE 3

Buffers tested

| Buffer | Composition | Concentrations tested | pH tested |
|---|---|---|---|
| Citrate | Trisodium citrate dihydrate | 5 to 25 mM | 2.6 to 3.6 |
| Maleate | Maleic acid, 0.5M NaOH | 5 to 25 mM | 2.6 to 3.6 |
| Acetate | Sodium acetate dihydrate | 5 to 25 mM | 2.6 to 3.6 |
| Formate | Sodium formate | 5 to 25 mM | 2.6 to 3.6 |

Analysis of the Appearance of the Eluate

Once the eluate is neutralized, a visual analysis is carried out by the operator using the following assessment scale: 0-Clear appearance; 1-Visible mild turbidity; 2-Moderate turbidity; 3-High turbidity (Opalescence). The neutralized eluate is then kept at room temperature for 1 hour. A second observation is carried out by the same operator using the same assessment scale.

Analysis of the Percentage of Monomeric IgG

A volume of 500 μL of the neutralized eluate is analyzed by high-performance liquid chromatography/size-exclusion chromatography (HPLC-SEC) on a Superose 12 column. The peaks generated by reading of the optical density at 280 nm are integrated by the Breeze software and the areas transformed into percentages.

Results

Comparison of Four Protein A Affinity Chromatography Resins

The results obtained for the four columns tested are presented in FIG. 1.

FIG. 1A shows that for the MabSelectSuRe™ column, a volume of 47 mL was injected onto the column until an OD at 280 nm of 66.4 mAU was obtained. The column binding capacity at 10% of BT ($DBC_{10\% \, BT}$) is thus 23 mg/mL of MabSelect SuRe™ gel.

Figure 1B:
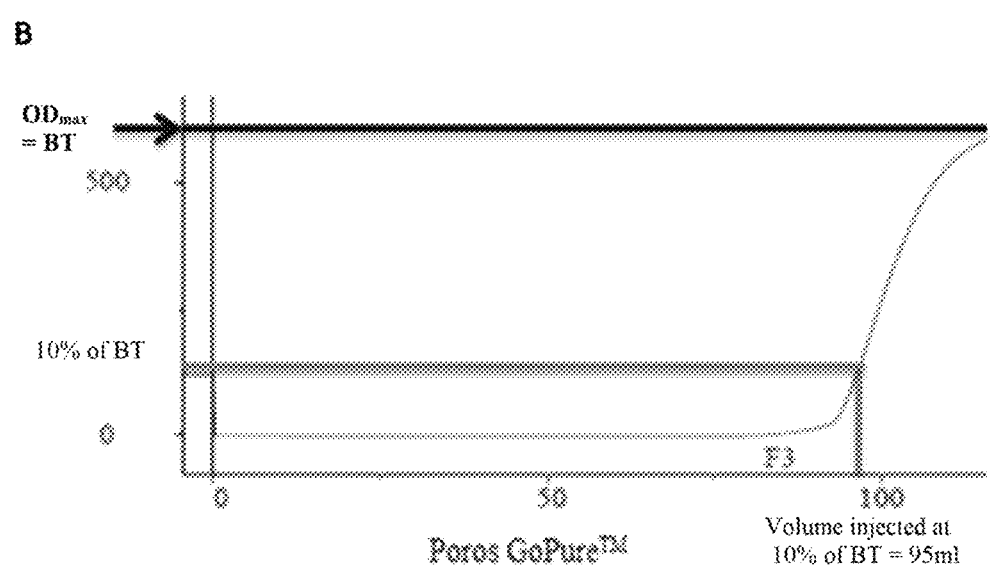

FIG. 1B shows that for the Poros GoPure™ column, a volume of 95 mL was injected onto the column until an OD at 280 nm of 66.4 mAU was obtained. The column binding capacity at 10% of BT ($DBC_{10\% \, BT}$) is thus 38.64 mg/mL of Poros GoPure™ gel.

Figures 1C, 1D:
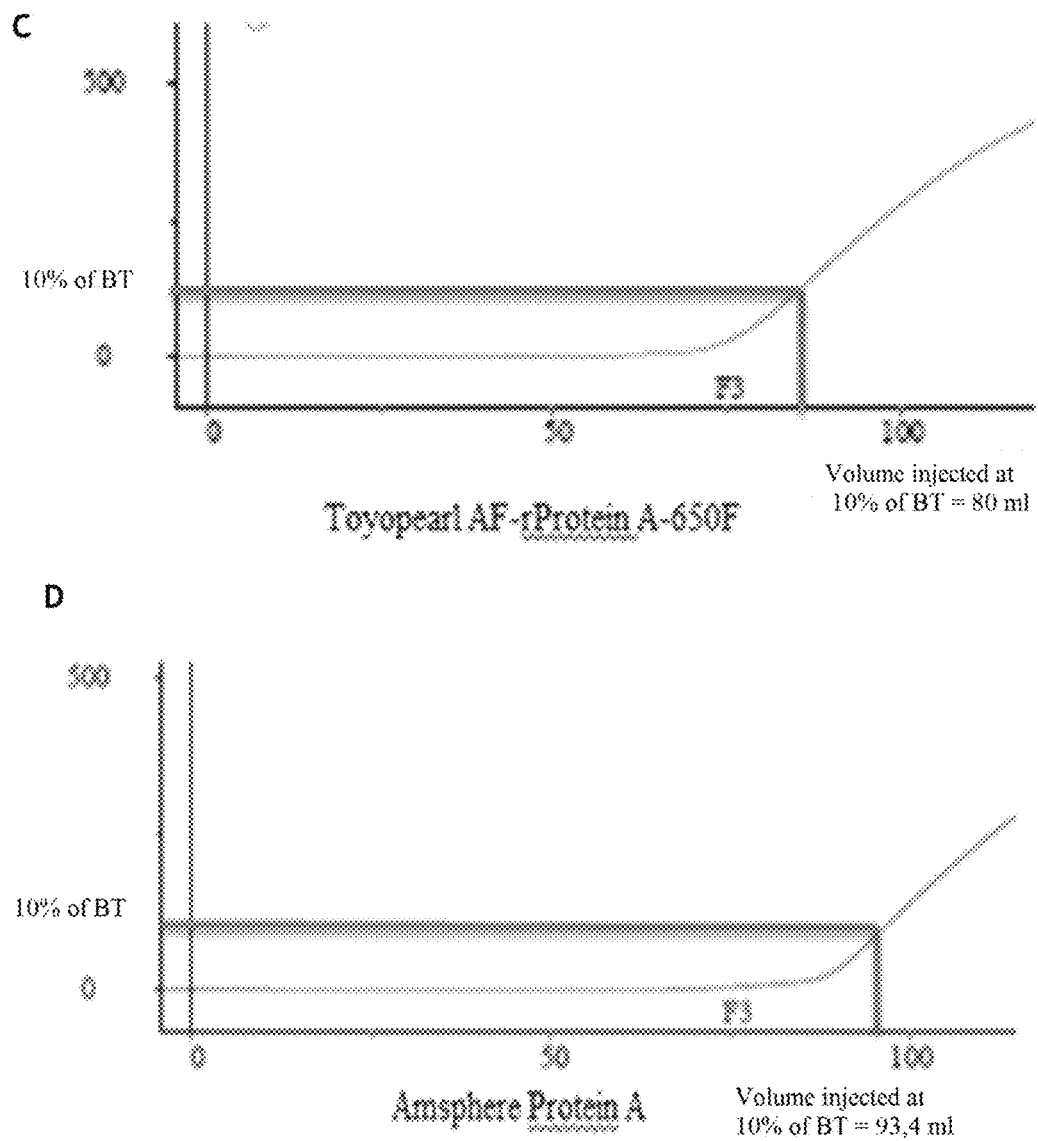
Figures 2A, 2B:
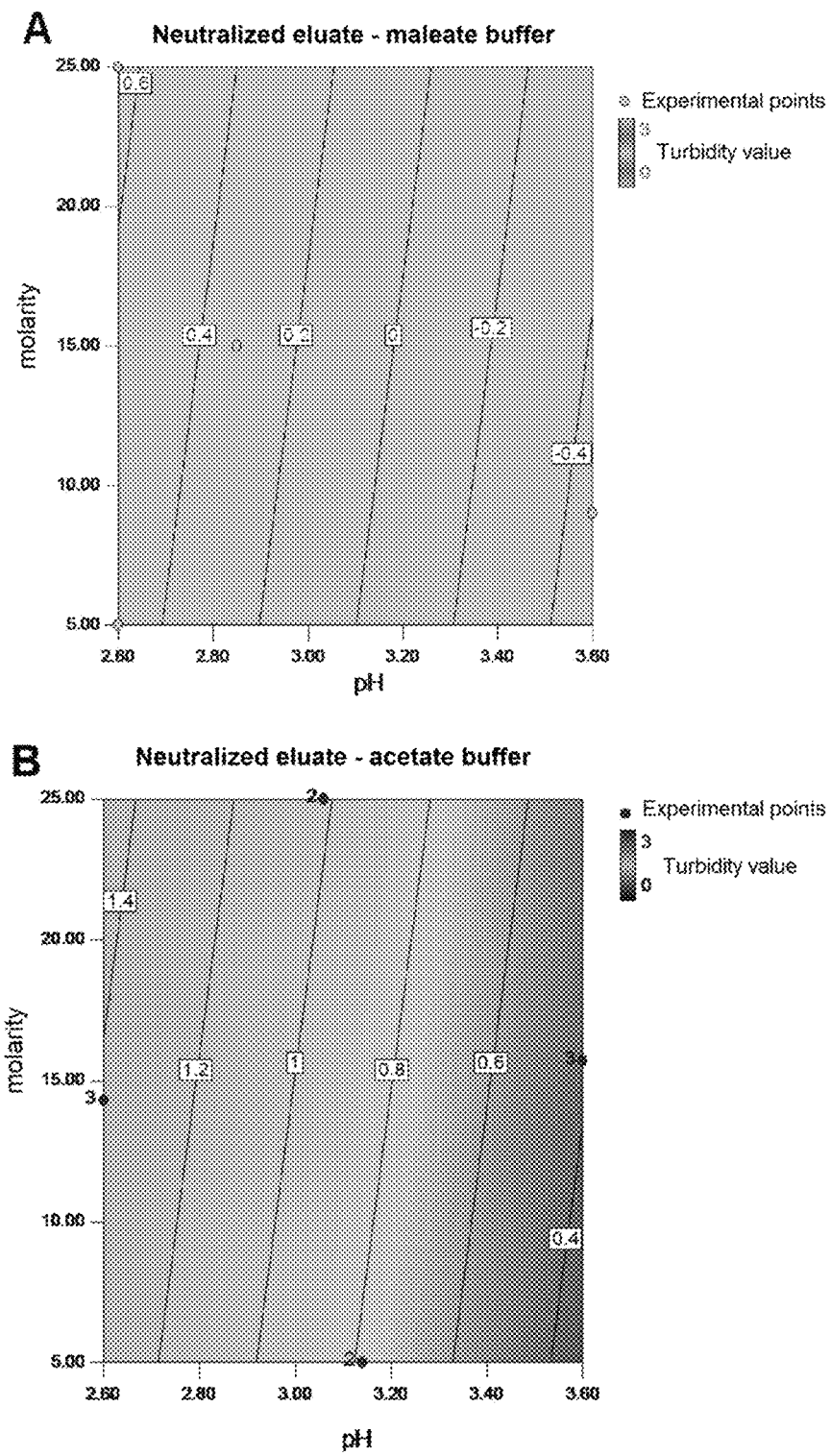
FIG. 2. Analysis by the Design-Expert® Software of the turbidity of the neutralized eluates (just after neutralization, A to D) and of the stabilized neutralized eluates (1 hour after neutralization, E to H) following elution of the protein A column with a maleate (A and E), acetate (B and F), formate (C and G) or citrate (D and H) buffer, as a function of the pH (represented on the X-axis) and the molarity (represented on the Y-axis) of the buffer. For a given pair (pH/molarity), the turbidity of each eluate is assigned a value varying between 0 and 3, a value of 0 corresponding to a clear eluate and a value of 3 to a very turbid eluate (opalescent). The curves representing the pairs (pH/molarity) corresponding to a given turbidity value are represented.
Figure 2C:
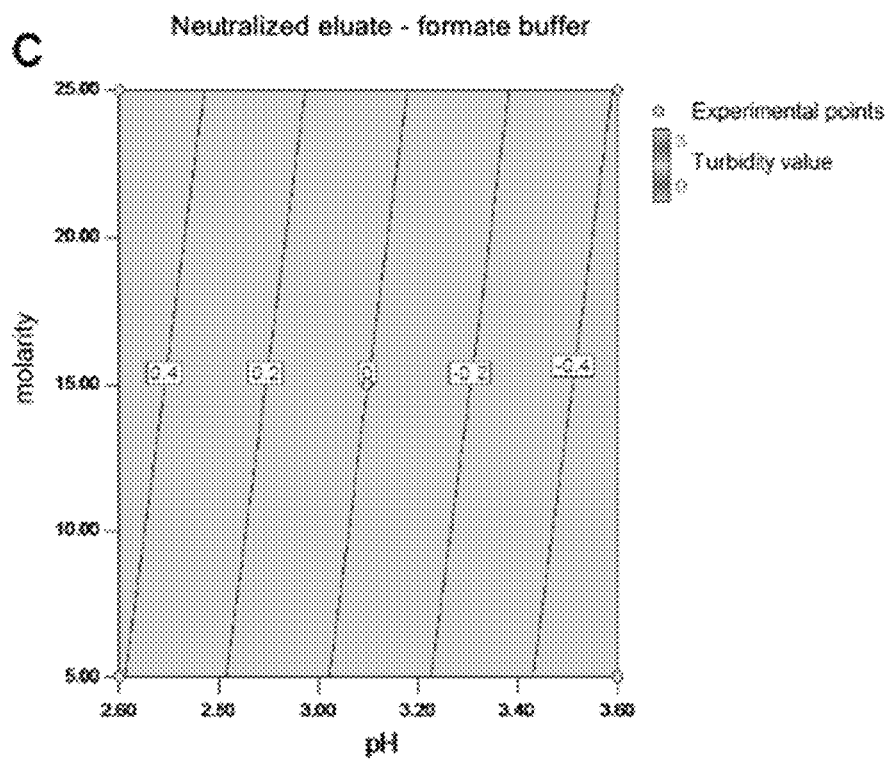
Figure 2D:
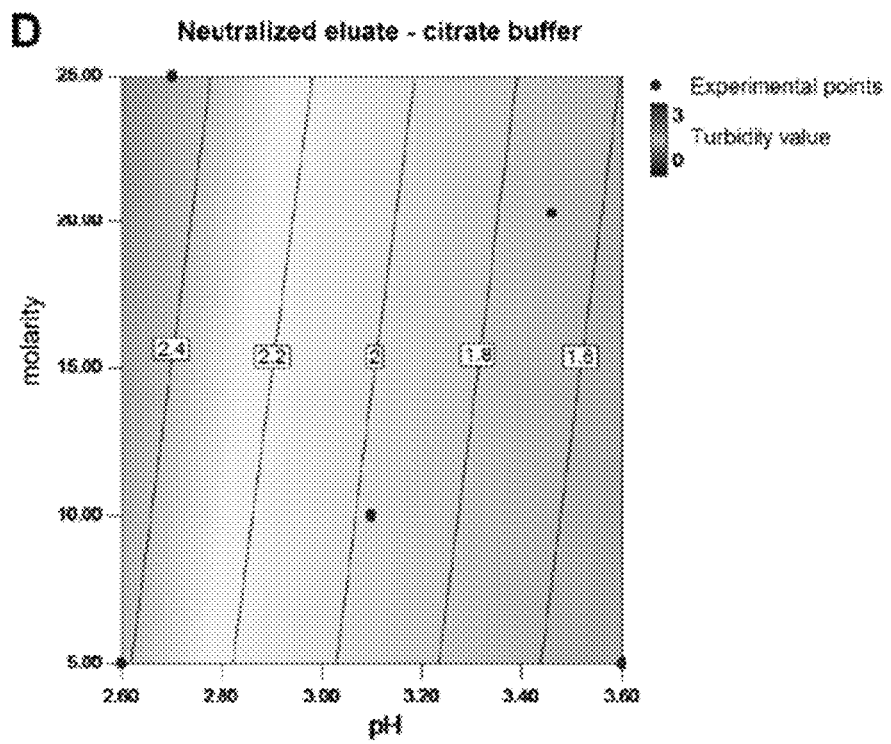
Figure 2E:
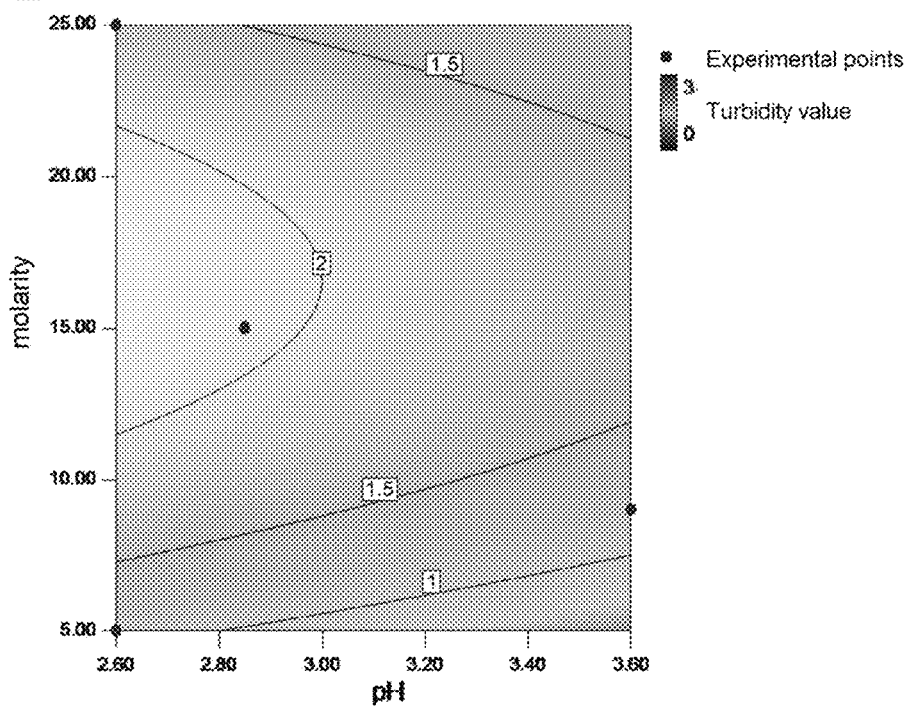
Figure 2F:
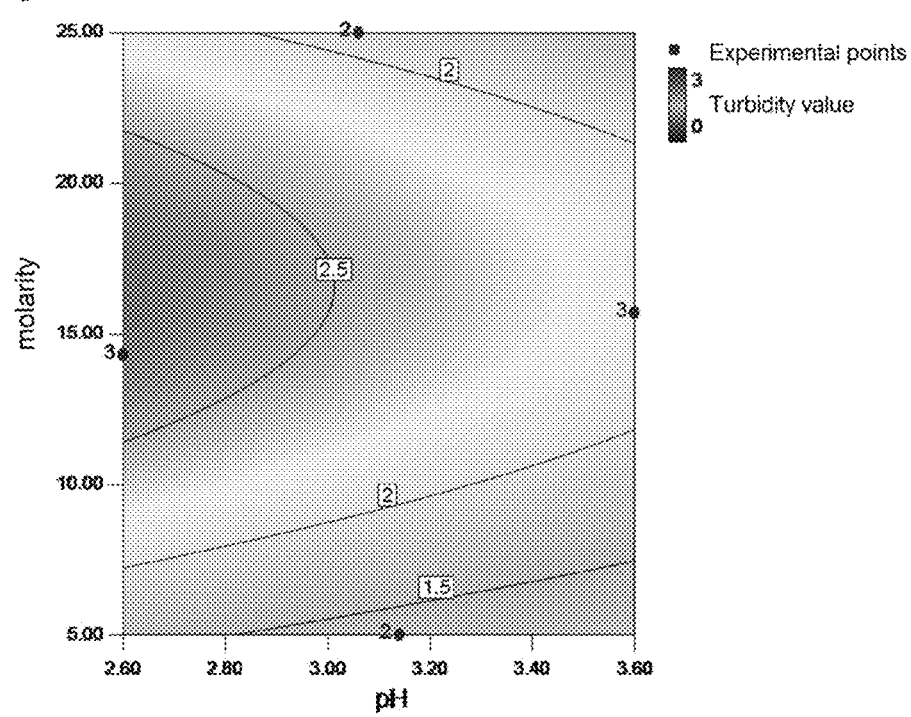
Figure 2G:
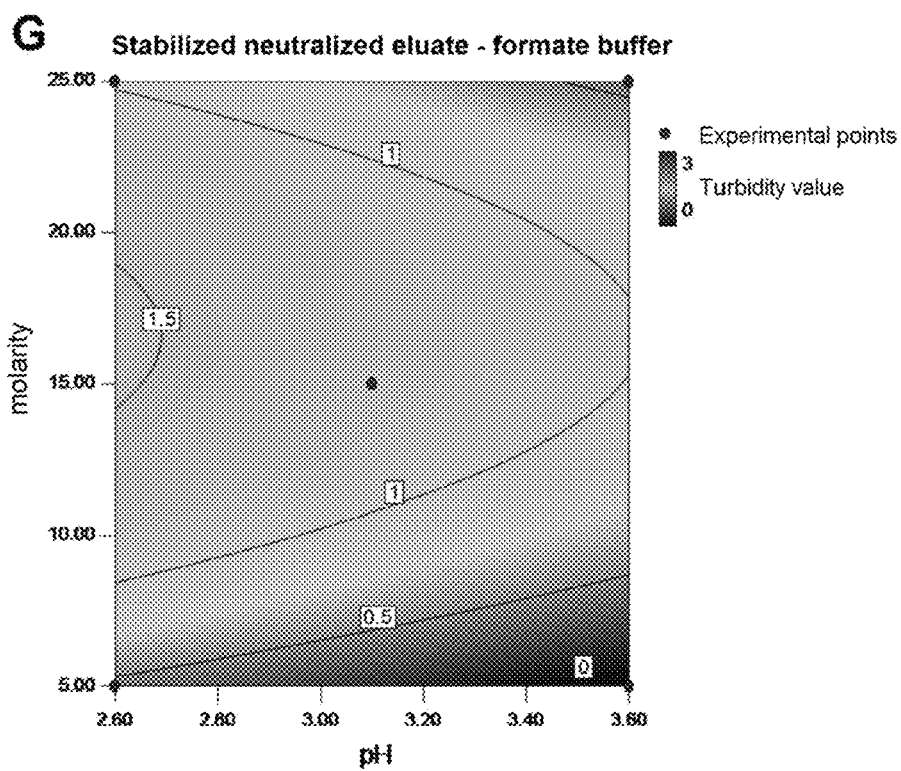
Figure 2H:
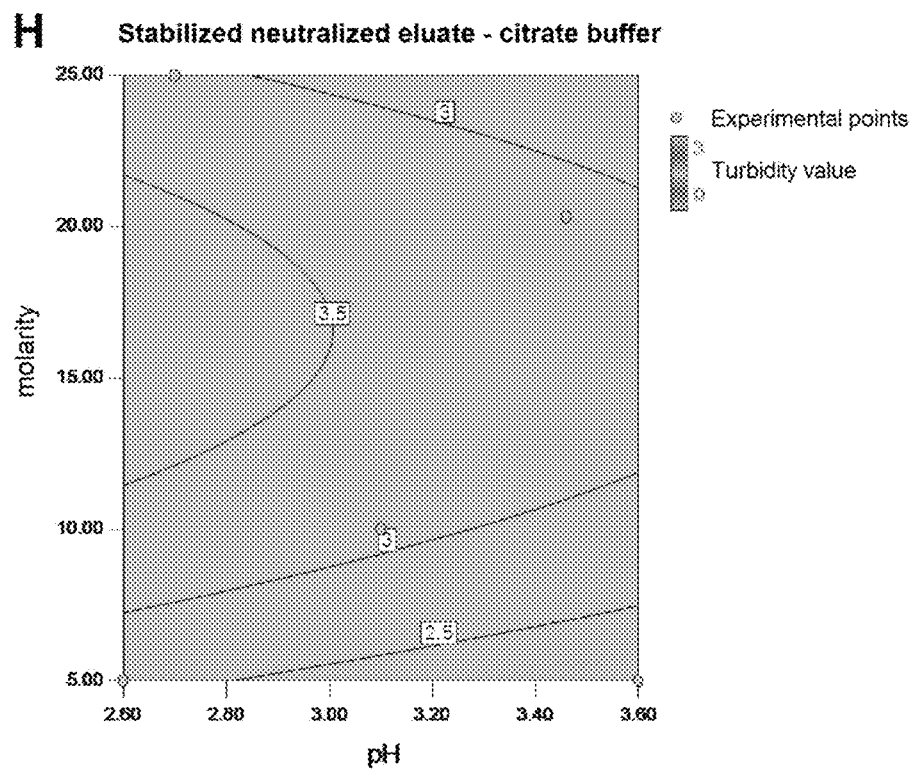

FIG. 1C shows that for the Toyopearl AF-rProtein A-650F column, a volume of 80 mL was injected onto the column until an OD at 280 nm of 66.4 mAU was obtained. The column binding capacity at 10% of BT ($DBC_{10\% \, BT}$) is thus 36.65 mg/mL of Toyopearl AF-rProtein A-650F gel.

FIG. 1D shows that for the Amsphere™ Protein A JWT203 column, a volume of 93.4 mL was injected onto the column until an OD at 280 nm of 66.4 mAU was obtained. The column binding capacity at 10% of BT ($DBC_{10\% \, BT}$) is thus 42.95 mg/mL of Amsphere™ Protein A JWT203 gel.

Table 4 below summarizes the data obtained with the four columns and shows that the Poros GoPure™ (cross-linked poly(styrene-divinylbenzene) matrix coated with cross-linked polyhydroxylated polymer), Toyopearl AF-rProtein A-650F (methacrylic polymer matrix) and Amsphere™ Protein A JWT203 (methacrylic polymer matrix) columns accept a significantly larger antibody load than the MabSelect SuRe™ column (highly cross-linked agarose matrix).

TABLE 4

Antibody load accepted by the various columns tested.

| Column | Volume injected at 10% of $OD_{max}$ (10% BT) | $DBC_{10\% \, BT}$ (in mg/mL of gel) | 90% of $DBC_{10\% \, BT}$ (in mg/mL of gel) |
|---|---|---|---|
| MabSelect SuRe ™ | 47 | 23 | 21 |
| Poros GoPure ™ | 95 | 38.64 | 35 |
| Toyopearl AF-rProtein A-650F | 80 | 36.65 | 33 |
| Amsphere ™ Protein A JWT203 | 93.37 | 42.95 | 39 |

In order to confirm the maximum load of the three columns permitting the largest antibody load, filtered and clarified supernatant was injected onto each column with an antibody load equal to 90% of the $DBC_{10\% \, BT}$ value. The loads thus applied are as follows:

TABLE 5

Loads applied to the various columns

| Column | 90% of $DBC_{10\% \, BT}$ |
|---|---|
| Poros GoPure ™ | 35 mg/mL |
| AF-rProtein A-650F | 33 mg/mL |
| Amsphere ™ Protein A JWT203 | 39 mg/mL |

Two tests were carried out for each of the three columns tested.

The results obtained are summarized in Table 6 below and show that the Amsphere™ Protein A JWT203 column gives the best results, in terms of antibody load as well as of purity, of appearance of the eluate, and even of the pH of the eluate (the latter being then adjusted to a pH of about 6.0 for the remainder of the method). Furthermore, the yield of this column is similar to that of the other columns.

Although the antibody load accepted by the Toyopearl AF-rProtein A-650F column is slightly less than that of the Amsphere™ Protein A JWT203 column, it nevertheless permits an antibody load greater than 30 mg/mL of gel and provides satisfactory results in terms of purity, of appearance of the eluate, and of the pH of the eluate.

Although permitting a large antibody load (at least 35 mg/mL of gel), the Poros GoPure™ column, in turn, results in poorly performing eluates, all of which appeared turbid. Moreover, the results are poorer in terms of yield and of purity.

TABLE 6

Comparison of three protein A affinity chromatography columns

| Column | Injection* (mg/mL of gel) | Test | Eluate volume | Appearance of the eluate | pH of the eluate | Yield | Purity |
|---|---|---|---|---|---|---|---|
| Poros GoPure ™ | 35 mg/mL | 1 | 3.3 | Turbid | 3.52 | 95.23 | 83.95% |
|  |  | 2 | 2.7 | Very turbid | 3.75 | 89.2 | 92.52% |
| Toyopearl AF-rProtein A-650F | 33 mg/mL | 1 | 3.2 | Clear | 3.82 | 94.48 | 94.00% |
|  |  | 2 | 2.2 | Opalescent | 4.88 | 100 | 93.13% |
| Amsphere ™ Protein A JWT203 | 39 mg/mL | 1 | 3.2 | Clear | 4.36 | 91.96 | 95.48% |
|  |  | 2 | 3 | Clear | 4.78 | 97.5 | 95.88% |

*Load corresponding to 90% of dynamic binding capacity (DBC) at 10% of breakthrough (BT)

Compared with the MabSelect SuRe™ gel commonly used in the first step of antibody purification by protein A affinity chromatography, the Amsphere™ Protein A JWT203 gel is a product whose price per liter is half as expensive and whose load capacity is about two times higher. This column thus makes it possible to decrease by a factor of four the cost of the first step of purification by protein A affinity chromatography.

Comparison of Four Elution Buffers

The results concerning the appearance of the eluate are presented in FIG. 2 and show that the maleate and formate buffers make it possible to obtain a clear or slightly opalescent stabilized, neutralized eluate for concentrations of between 5 and 10 mM (particularly at 5 mM) and a pH of between 2.6 and 3.6.

The acetate buffer does not make it possible to obtain clear eluates and can even lead, at low pH and moderate molarity, to very turbid eluates 1 hour after neutralization. As for the citrate buffer, the results are very poor in terms of appearance for the stabilized, neutralized eluate.

Figures 3A, 3B:
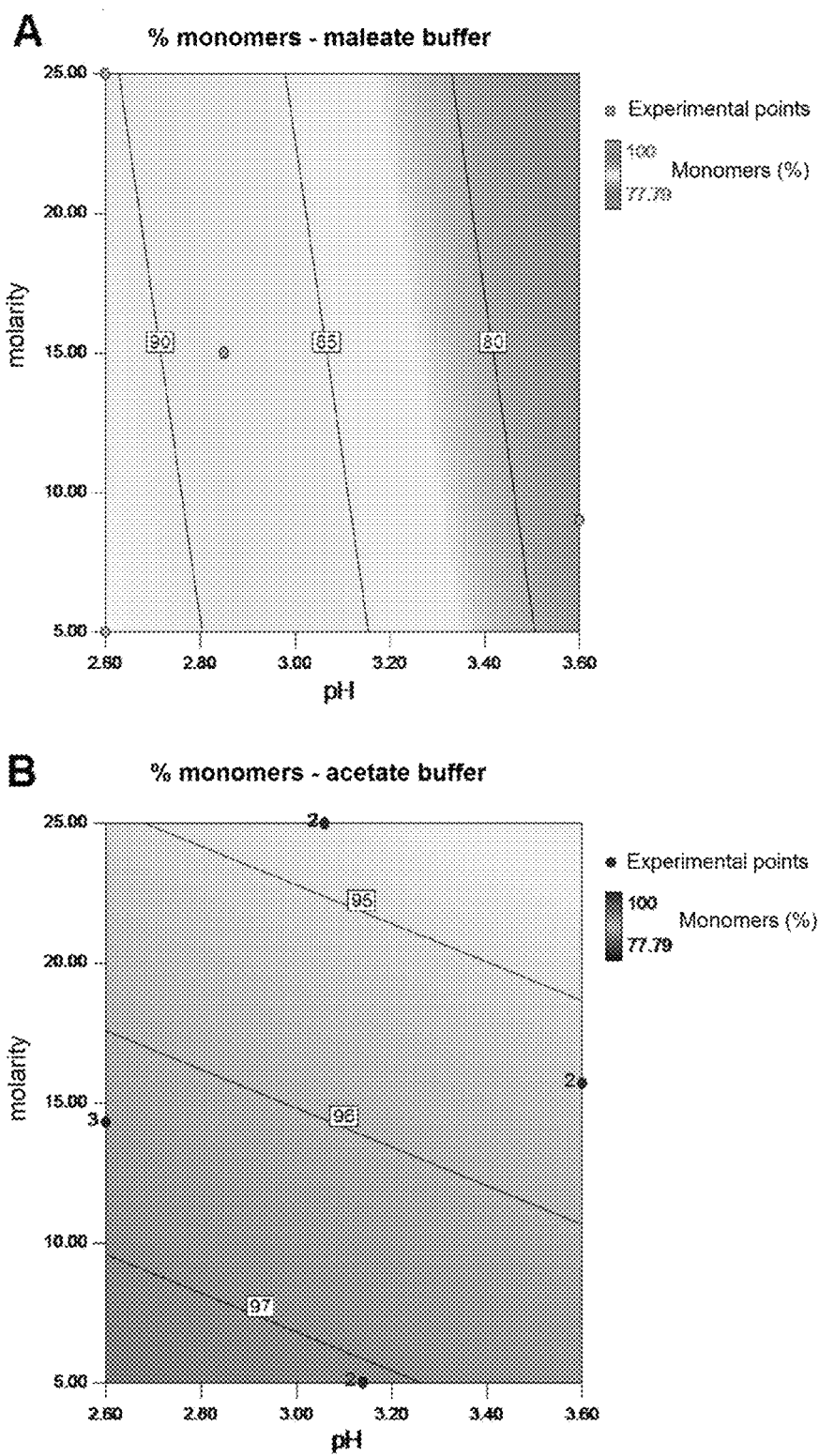
FIG. 3. Analysis of the percentage of monomers in neutralized eluates following elution of the protein A column with a maleate (A), acetate (B), formate (C) or citrate (D) buffer, as a function of the pH (represented on the X-axis) and the molarity (represented on the Y-axis) of the buffer. The curves representing the pairs (pH/molarity) corresponding to a percentage value of monomeric forms of the antibody in the neutralized eluate are represented.
Figures 3C, 3D:
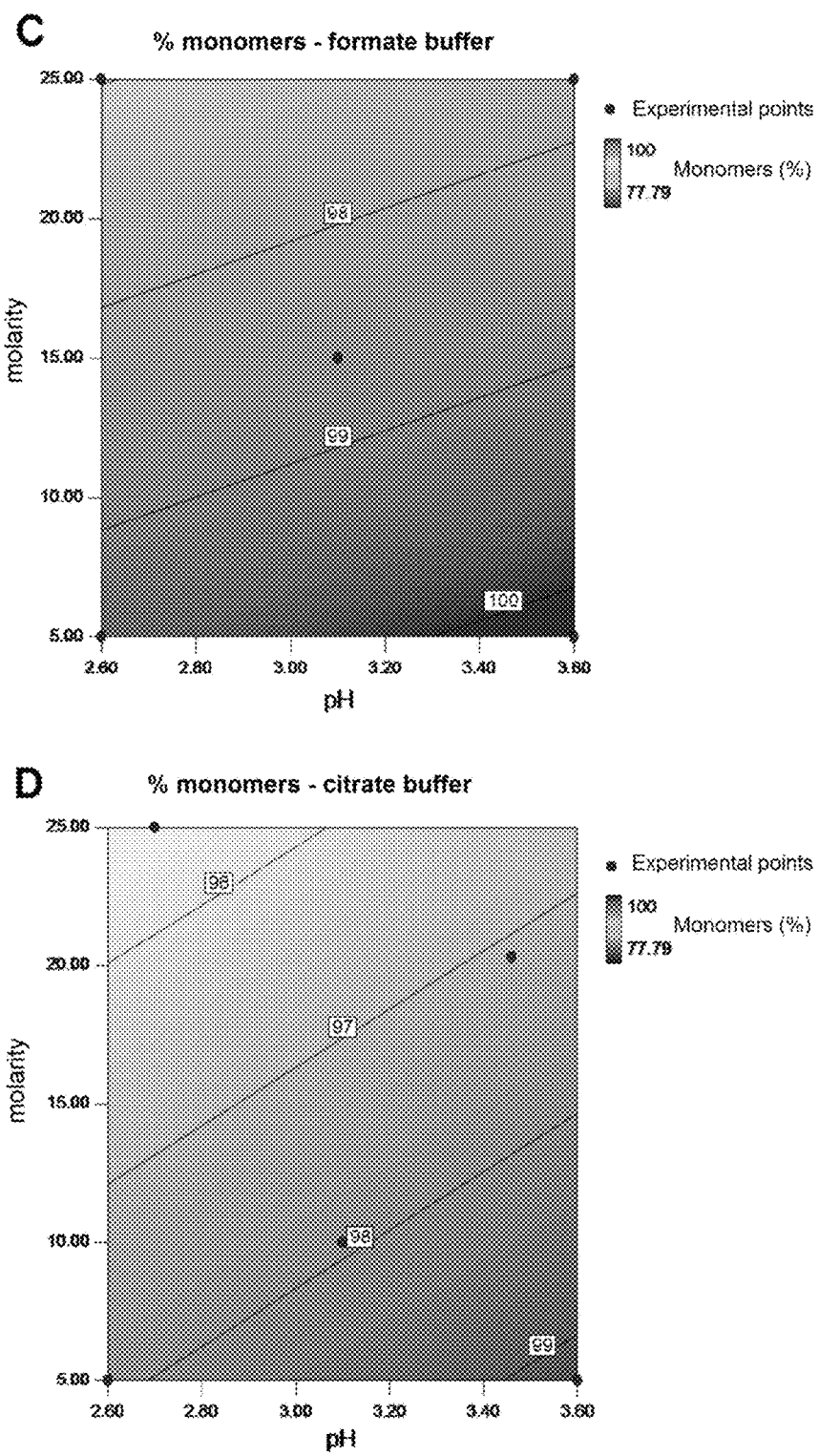

The results concerning the percentage of monomeric forms of the antibody in the neutralized eluate are presented in FIG. 3, and show that more than 98% of the antibodies are in monomeric form in the neutralized eluate after elution by a citrate or formate buffer at a molarity of 5 mM and a pH of between 2.6 and 3.6.

Although making it possible to obtain clear or only slightly opalescent eluates, the maleate buffer leads to a significant formation of antibody aggregates (always more than 5%), which is undesirable. As for the acetate buffer, the results are poorer than with a citrate or formate buffer.

Overall, the buffer providing the best results, in terms of the appearance of the neutralized eluate as well as of the percentage of the monomeric forms of antibody in the neutralized eluate, is the formate buffer, used preferably at a molarity of 5 to 10 mM (preferably 5 mM) and at a pH of between 2.6 and 3.6 (particularly at a pH of 3.1).

Conclusions

Compared with the MabSelect SuRe™ gel commonly used in the first step of antibody purification by protein A affinity chromatography, the inventors were able to select a column making it possible to decrease by a factor of four the cost of the first step of purification by protein A affinity chromatography, while maintaining the purity and the quality of the purified product.

Moreover, the inventors also selected a particularly advantageous elution buffer to guarantee a clear or slightly opalescent neutralized eluate and comprising a very large majority of monomeric forms of the antibody.

The specific combination of column and of buffer selected by the inventors thus makes it possible to substantially reduce the cost of the purification while guaranteeing a product of high purity and quality.

Example 2: Optimization of the Cation-Exchange Chromatography Step c)

A virally inactivated eluate derived from step b) of the method was purified by cation-exchange chromatography on two different types of columns: an SP Sepharose column and a Capto™ S column.

Materials and Methods

Cation-Exchange Chromatography on SP Sepharose®

A virally inactivated eluate derived from step b) of the method was adjusted to 50 mOsm/kg and pH 7.2, and was injected onto an SP Sepharose® column at a load of about 30.5 g/L of gel according to the sequence:

TABLE 7

Purification sequence for a virally inactivated eluate derived from step b) of the method according to the invention by cation-exchange chromatography on SP Sepharose ®

| Designation | Solution/Buffer used | Flow rate | Minimum volume of buffer | Controlled parameters |
|---|---|---|---|---|
| Removal of storage solution | Purified water | ≤200 cm/h | 2CV | NA |
| Equilibration | 20 mM sodium phosphate buffer, pH 7.2, 50 mOsm/kg | ≤200 cm/h | 5CV | pH and osmolality |
| Injection | Inactivated product adjusted to 50 mOsm/kg and pH 7.2 | ≤200 cm/h | About 5 liters | NA |
| Return to baseline | 20 mM sodium phosphate buffer, pH 7.2, 50 mOsm/kg | ≤200 cm/h | 5CV | OD |
| Flow reversal on the column | | | | |
| Removal of the solvent-detergent | 20 mM sodium phosphate buffer, pH 7.2, 50 mOsm/kg | ≤200 cm/h | 14CV | NA |
| Elution | 20 mM sodium phosphate, 150 mM NaCl buffer, pH 7.2, 50 mOsm/kg | ≤200 cm/h | 4CV | Collect at OD ≥ 0.2 AU |

Cation-Exchange Chromatography on Capto™ S $1^{st}$ Test, in Parallel with SP Sepharose®

A virally inactivated eluate derived from step b) of the method was adjusted to 5.09 mS/cm by the addition of sodium acetate buffer (5 mM, pH 6.0), and to pH 5.98, and was injected onto a Capto™ S column at a load of about 67.3 g/L of gel according to the sequence:

TABLE 8

Purification sequence for a virally inactivated eluate derived from step b) of the method according to the invention by cation-exchange chromatography on Capto™ S

| Designation | Solution/Buffer | Flow rate | Minimum volume of buffer | Controlled parameters |
|---|---|---|---|---|
| Removal of storage solution | Purified water | 8 mL/min or 240 cm/h | 2CV | NA |
| Equilibration | 20 mM sodium acetate, QS NaCl, conductivity 5 mS/cm, pH 6.0 | Residence time 3 min | Until equilibration | pH and conductivity |
| Injection | Inactivated protein A eluate | | 365 mL (67.3 g/L) | OD at 280 nm |
| Return to baseline | 20 mM sodium acetate, QS NaCl, conductivity 5 mS/cm, pH 6.0 | | 2CV | OD at 280 nm |
| Direction of injection | | Flow reversal | | |
| Wash | 20 mM sodium acetate, QS NaCl, conductivity 5 mS/cm, pH 6.0 | 8 mL/min or 240 cm/h | 14CV | OD at 280 nm |
| Elution | 20 mM Tris, QS NaCl, conductivity 18 mS/cm, pH 7.0 | | 10CV | Collect at 250 mAU OD at 280 nm |

$2^{nd}$ Test

A virally inactivated eluate derived from step b) of the method was adjusted to 5.04 mS/cm by addition of 103.8 mL of purified water and to pH 6.02 by addition of 0.5 M NaOH.

For this step, the Capto S gel is packed in a 1 cm-diameter column, thus obtaining a column volume of 4.8 mL with a height of 6.1 cm.

The injection onto the Capto S cation-exchange column proceeded as follows:

TABLE 9

Purification sequence for a virally inactivated eluate derived from step b) of the method according to the invention by cation-exchange chromatography on Capto ™ S in a second test.

| Designation | Solution/Buffer | Flow rate | Minimum volume of buffer/solution | Controlled parameters |
|---|---|---|---|---|
| Removal of storage solution | Purified water | ≤600 cm/h | 2CV | NA |
| Equilibration | 20 mM sodium phosphate, QS NaCl, conductivity 5 mS/cm, pH 6.0 | ≤600 cm/h | Until equilibration | pH and conduction |
| Injection | Protein A eluate | ≤600 cm/h | According to the [ ] of IgG | OD at 280 nm |
| Return to baseline | 20 mM sodium phosphate, QS NaCl, conductivity 5 mS/cm, pH 6.0 | ≤600 cm/h | 2CV | OD at 280 nm |
| Direction of injection | | Flow reversal | | |
| Wash | 20 mM sodium phosphate, QS NaCl, conductivity 5 mS/cm, pH 6.0 | ≤600 cm/h | 14CV | OD at 280 nm |
| Flow reversal, downflow passage | | | | |
| Elution | 20 mM sodium phosphate, QS NaCl, conductivity 18 mS/cm, pH 6.9 | ≤400 cm/h | 10CV | Collect at 250 mAU OD at 280 nm |

The column is loaded in an amount of 120 grams of IgG/L of gel in order to determine the maximum binding capacity of the Capto S gel.

Determination of the Breakthrough Point and the Dynamic Binding Capacity at 10% Passage ($DBC_{10\%\ BT}$)

A virally inactivated eluate derived from step b) of the method was adjusted to 5.05 mS/cm and to pH 6.04 by addition of 6N HCl solution and apyrogenic purified water (APW).

For this step, Capto S gel is packed in a 0.5 cm-diameter column, thus obtaining a column volume of 3.8 mL with a height of 19.5 cm.

The antibody solution is then injected into the chromatography apparatus (Akta Basic) without passing through the column. The OD at 280 nm thus read corresponds to the maximum OD at 280 nm. The UV cell and the circuit of the apparatus are then rinsed with water then with equilibration buffer.

The dynamic binding capacity at 10% passage ($DBC_{10\%\ BT}$) was then determined for three residence times (1, 2 and 3 minutes) by injecting onto the column the antibody solution at various flow rates (3.8 mL/min, 1.9 mL/min, and 1.3 mL/min, respectively) and by monitoring the OD at 280.

Results

Comparison of Cation-Exchange Chromatography on SP Sepharose® and Cation-Exchange Chromatography on Capto™ s SP Sepharose®: the volume of eluate collected is 150 mL, with an estimated protein concentration of 25.96 g/L, an osmolality of 273 mOsm/kg and a pH of 7.09.

The quantity of antibody present in the eluate was 3894 mg. The step yield is 88.6%. The product is clear with a few particles.

Capto™ S: at the end of the elution, a volume of 174 mL (7.3 CV) is obtained. The final concentration of the eluate is 9.0 g/L, which has a clear appearance at the column outlet. The step yield is thus 94.3% and the pH and the conductivity of the eluate are respectively 6.66 and 17.11 mS/cm.

The eluate is then filtered on a 0.22 μm Millipak 20 capsule conditioned beforehand with 20 mM Tris, QS NaCl buffer, conductivity 18 mS/cm, pH 7.0. Filtration is carried out with an "L02" pump at a speed of 30 rpm via 184 tubing. The filter is then rinsed with 20 mM Tris, QS NaCl buffer, conductivity 18 mS/cm, pH 7.0. At the conclusion of this filtration, a volume of 208.8 mL is obtained with a concentration of 6.8 g/L and a filtration step yield of 90.7%. The purity of the filtered eluate is 99.6% (in proteins).

TABLE 10

Comparative data for purification by cation-exchange chromatography on SP Sepharose ® and Capto ™ S.

| Parameter analyzed | SP Sepharose ® | Capto ™ S |
|---|---|---|
| Antibody load | 30.5 g/L of gel | 67.3 g/L of gel |
| Volume eluted | 150 mL | 174 mL |
| Yield | 88.6% | 94.3% |
| Eluate appearance | Clear with a few particles | Clear |
| Purity | ND | 99.6% |

Table 10 above shows that the Capto™ S column permits an antibody load two times higher than the SP Sepharose® column (thus reducing costs), a better yield (thus reducing costs), while guaranteeing a clear appearance and a very good purity.

$2^{nd}$ Test of Cation-Exchange Chromatography on Capto™ S

The inflection point of the OD curve is at 110 mL; the OD at 280 nm, which up to that point was 1650 mAU, gradually increases, representing an escape of IgG through the column. This gives a maximum binding capacity of about 84 g/L.

At the end of the elution, a volume of 57.2 mL (11.9 CV) is obtained. The elution is initially very rapid but then lags over time (very slow decrease in OD at 280 nm). The final concentration of the eluate is 7.30 g/L, which has a clear appearance at the column outlet. However, particles appear after a few minutes.

The step yield, if based on 110 mL of product injected, is 100%.

Moreover, after cation-exchange chromatography on Capto S gel, the IgG solution appears 100% pure (in proteins).

Thus, this 2$^{nd}$ test confirms that the maximum antibody load of the Capto™ S column is much higher than that of the SP Sepharose® column.

Breakthrough (BT) Point and Dynamic Binding Capacity at 10% Passage (DBC$_{10\% BT}$) of the Capto™ S Column The maximum OD at 280 nm—read by injecting the antibody solution into the chromatography apparatus (Akta Basic) without passing through the column—is 535 mAU. The point corresponding to a 10% loss of load from the column, called "breakthrough" (10% BT), is thus determined at 54 mAU.

The measurement of dynamic binding capacity at 10% passage (DBC$_{10\% BT}$) for residence times of 1, 2 and 3 minutes gave the results presented in Table 11 below:

TABLE 11

Results of measurement of dynamic binding capacity at 10% passage (DBC$_{10\% BT}$) for residence times of 1, 2 and 3 minutes.

| Residence time (flow rate) | Volume injected at 10% of OD$_{max}$ (10% BT) | DBC$_{10\% BT}$ (in g/L of gel) | 90% of DBC$_{10\% BT}$ (in g/L of gel) |
|---|---|---|---|
| 1 minute (3.8 mL/min) | 207.8 | 87 | 78 |
| 2 minutes (1.9 mL/min) | 250.5 | 104 | 94 |
| 3 minutes (1.3 mL/min) | 265.6 | 111 | 100 |

These results confirm the much higher binding capacity of the Capto™ S column in relation to the SP Sepharose® column.

Conclusions

The selection by the inventors of the Capto™ S column for the cation-exchange chromatography step c), rather than the SP Sepharose® column commonly used in this antibody purification step, here again makes it possible to reduce purification costs.

Example 3: Optimization of the Nanofiltration Step e)

The nanofiltration step e) is essential for guaranteeing the viral safety of the final antibody composition, particularly with respect to small non-enveloped viruses. However, this step is also very expensive, as nanofilters are very expensive products. Since each nanofilter is used only once, the inventors tested several different nanofilters in order to optimize the antibody load that could be processed at one time, so as to reduce the cost of this step.

Moreover, the advantage of using a prefilter with a larger pore size to increase the antibody load was also studied.

Materials and Methods

Comparison of Three Different Filters

Starting Product

The Mustang Q filtrate (step d)) is diluted to ⅔ using trisodium citrate dihydrate (22.05 g/L), NaCl (18.23 g/L) buffer (pH 6.5, 800 mOsm/kg), for a final volume of 555 mL. 0.2 µm filtration is then carried out on a 0.02 m$^2$ Millipak 40 filter followed by rinsing with buffer K, for a final volume of 672 mL, a concentration of 5.28 g/L, a pH of 7.14 and an osmolality of 367 mOsm/kg.

The product is then filtered on a Pall 0.1 µm grade hydrophilic PVDF filter, followed by rinsing with buffer K, for a final volume of 643 mL, a concentration of 5.16 g/L, a pH of 7.12 and an osmolality of 366 mOsm/kg.

Filters Used

The characteristics of the nanofilters tested are as follows:

TABLE 12

Characteristics of the filters tested

| Filter | Manufacturer | Membrane | Pore size |
|---|---|---|---|
| Planova® 15N | Asahi Kasei | hollow fibers of cuprammonium- regenerated cellulose | 15 ± 2 nm |
| Planova® 20N | | | 19 ± 2 nm |
| Viresolve Pro 20N | Millipore | dual asymmetrical polyethersulfone membrane | About 20 nm |

Nanofiltration on Planova® 15N

The nanofiltration step is carried out on a 0.001 m$^2$ Planova® 15N filter equilibrated with trisodium citrate (7.35 g/L), NaCl (9 g/L) buffer (pH 6.5, 360 mOsm/kg) at a pressure of 300±50 mbar. The average rate was 0.15 mL/min. The filtrate was clear at the end of the nanofiltration.

Nanofiltration on Planova® 20N

The nanofiltration step is carried out on a 0.001 m$^2$ Planova® 20N filter equilibrated with trisodium citrate (7.35 g/L), NaCl (9 g/L) buffer (pH 6.5, 360 mOsm/kg) at a pressure of 800±50 mbar.

Nanofiltration on Viresolve Pro 20N

The nanofiltration step is carried out on a 3.1 cm$^2$ Viresolve Pro 20N filter equilibrated with trisodium citrate (7.35 g/L), NaCl (9 g/L) buffer (pH 6.5, 360 mOsm/kg) at a pressure of 2 bar.

Validation of the Use of the Viresolve Pro 20N Filter

The Viresolve Pro 20N filter was tested on several purified antibody compositions, in order to validate the antibody load that can be filtered at one time.

Test 1

The totality of the cation-exchange chromatography eluate (step c) of the method according to the invention) was filtered on a 0.22 µm Mini Kleenpak capsule rinsed using 20 mM phosphate buffer, pH 6.9, conductivity 5 mS/cm. At the conclusion of this filtration, a volume of 64.3 mL is obtained with a concentration of 5.9 g/L. The filtration yield is 90.7%, which is explained by the fact that the filter was rinsed with little buffer to avoid having the IgG concentration drop too low for the following nanofiltration step. The product is stable after 0.22 µm filtration. It is then stored for 24 hours at +4° C.

The 64.3 mL of starting material was injected at 2 bar onto the 3.1 cm$^2$ Viresolve Pro+ nanofilter equilibrated with 20 mM sodium phosphate buffer, conductivity 5 mS/cm, pH 6.9. The appearance of the product stored for 24 hours at +4° C. before nanofiltration was clear. The nanofiltration step was thus carried out directly on the product without prior 0.1 µm filtration.

Test 2

The appearance of the product derived from the anion-exchange chromatography on Mustang Q (step d) of the method according to the invention), subjected to a dialysis step and stored for 24 hours at +4° C., was clear. Before nanofiltration, the latter was filtered on a 0.1 µm Mini Kleenpak capsule rinsed using trisodium citrate dihydrate (8.82 g/L), NaCl (3.25 g/L), mannitol (17 g/L) buffer, pH 6.5, 300 mOsm/kg. At the conclusion of this filtration, a volume of 264 mL is obtained with a concentration of 5.1 g/L. The filtration yield is 100%.

The filtered dialyzed solution is injected at 2 bar onto the 3.1 cm² Viresolve® Pro nanofilter equilibrated beforehand with trisodium citrate dihydrate (8.82 g/L), NaCl (3.25 g/L), mannitol (17 g/L) buffer, pH 6.5, 300 mOsm/kg.

Test 3

The Mustang Q® eluate (step d) of the method according to the invention) is injected at 2 bar onto the 3.1 cm² Viresolve® Pro nanofilter equilibrated beforehand with 20 mM Tris buffer, pH 6.5, 10 mS/cm.

Use of a Prefilter

The nanofiltration of the same Mustang® Q eluate (step d) of the method according to the invention) directly on the Viresolve® Pro filter or after passing through a Sartorius® or Millipore® prefilter was tested.

Direct Nanofiltration

The Mustang® Q eluate (step d) of the method according to the invention) is injected at 2 bar onto the 3.1 cm² Viresolve® Pro nanofilter equilibrated beforehand with 20 mM Tris buffer, pH 6.5, 10 mS/cm. This experiment corresponds to test 3 above of the Viresolve® Pro filter.

Nanofiltration after Passing Through a Sartorius® Prefilter

A Sartorius® prefilter is connected in series with the Viresolve® Pro nanofilter. The Mustang® Q eluate (step d) of the method according to the invention) is injected at 2 bar onto the 3.1 cm² Viresolve® Pro nanofilter equilibrated beforehand with 20 mM Tris buffer, pH 6.5, 10 mS/cm.

Nanofiltration after Passing Through a Millipore® Prefilter

A Millipore® prefilter (OptiScale®-40 Viresolve prefilter ref. SSPVA40NB9) is connected in series with the 3.1 cm² Viresolve® Pro nanofilter. The Mustang® Q eluate is injected at 2 bar onto the 3.1 cm² Viresolve® Pro nanofilter equilibrated beforehand with 20 mM Tris buffer, pH 6.5, 10 mS/cm.

Nanofiltration after Passing Through a Millipore® Prefilter (Validation on a 2$^{nd}$ Product)

A Millipore prefilter (Viresolve Pro ref. C2NA74678) is connected in series with the 3.1 cm² Viresolve Pro nanofilter. The product derived from the anion-exchange chromatography on Mustang Q (step d) of the method according to the invention) and from the dialysis step is injected at 2 bar onto the 3.1 cm² Viresolve Pro+ assembly equilibrated beforehand with trisodium citrate dihydrate (8.82 g/L), NaCl (3.25 g/L), mannitol (17 g/L) buffer, pH 6.5.

Nanofiltration after Passing Through a Millipore® Prefilter (Validation on a 2$^{nd}$ Product)

Two Millipore prefilters (Viresolve Pro Shield ref. C2NA74678) are connected in parallel upstream of the 3.1 cm² Viresolve Pro nanofilter. The assembly is equilibrated beforehand in its entirety under a pressure of 2 bar with APW then with trisodium citrate dihydrate (8.82 g/L), NaCl (3.25 g/L), mannitol (17 g/L) buffer, pH 6.5. The second prefilter remains clamped at the beginning of the injection of the product, and is unclamped in the event the first prefilter is filled. This assembly makes it possible to determine the Vmax of the nanofilter without the prefilter being potentially limiting.

Figure 4A:
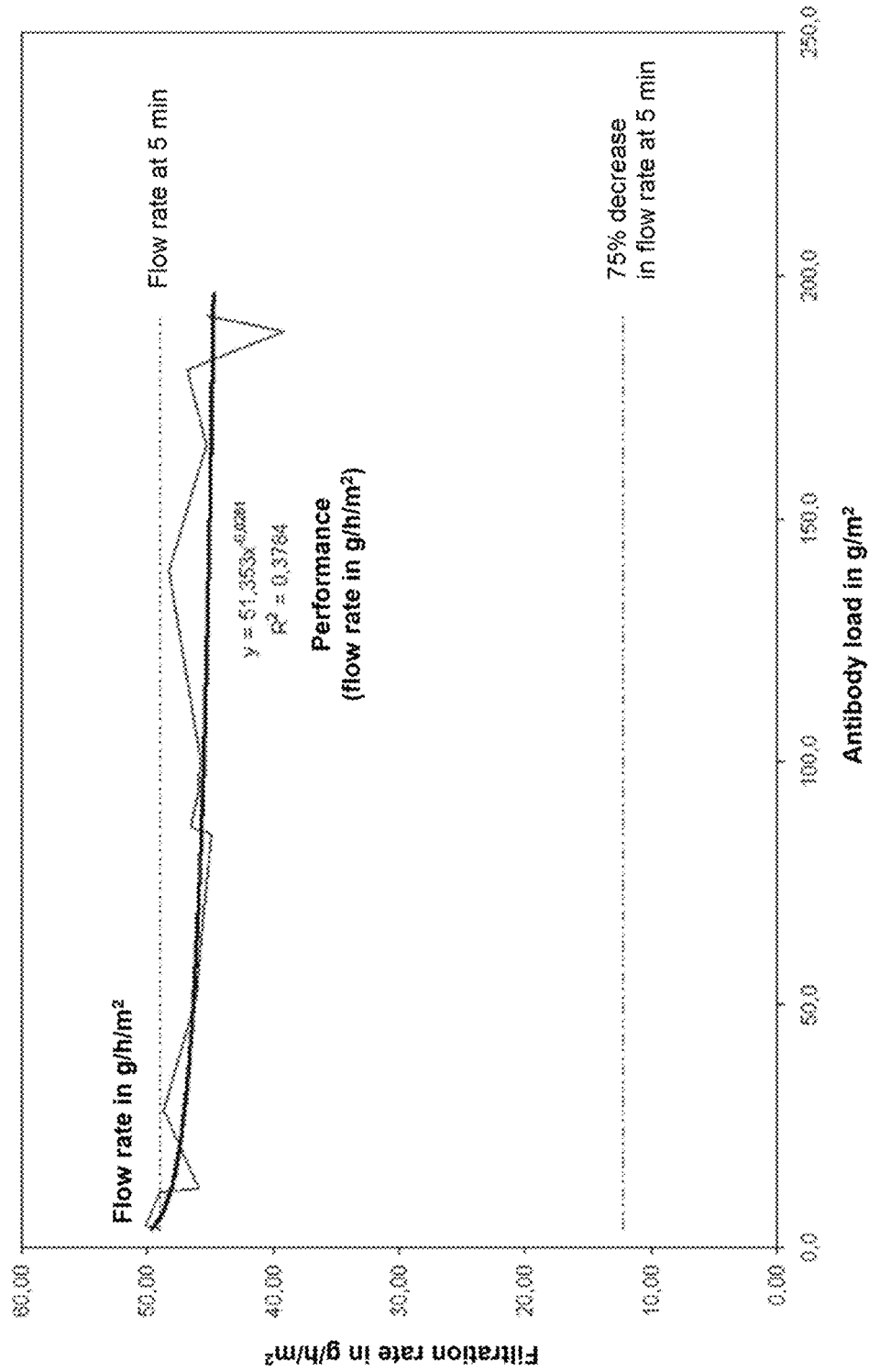
FIG. 4. Filtration rate (g/h/m²) as a function of antibody load (g/m²) for nanofiltration on a Planova® 15N (A), Planova® 20N (B) or Viresolve® Pro 20N (C) filter.

Average rate over 10 min with APW=2.18 g/min
Average rate over 10 min in citrate buffer=2.52 g/min Results Comparison of Three Different Filters Nanofiltration on Planova® 15N FIG. 4A represents filtration rate as a function of antibody load. The average rate was 0.15 mL/min for an antibody load ranging up to nearly 200 g/m². The filtrate was clear at the end of the nanofiltration.

Nanofiltration on Planova® 20N

Figure 4B:
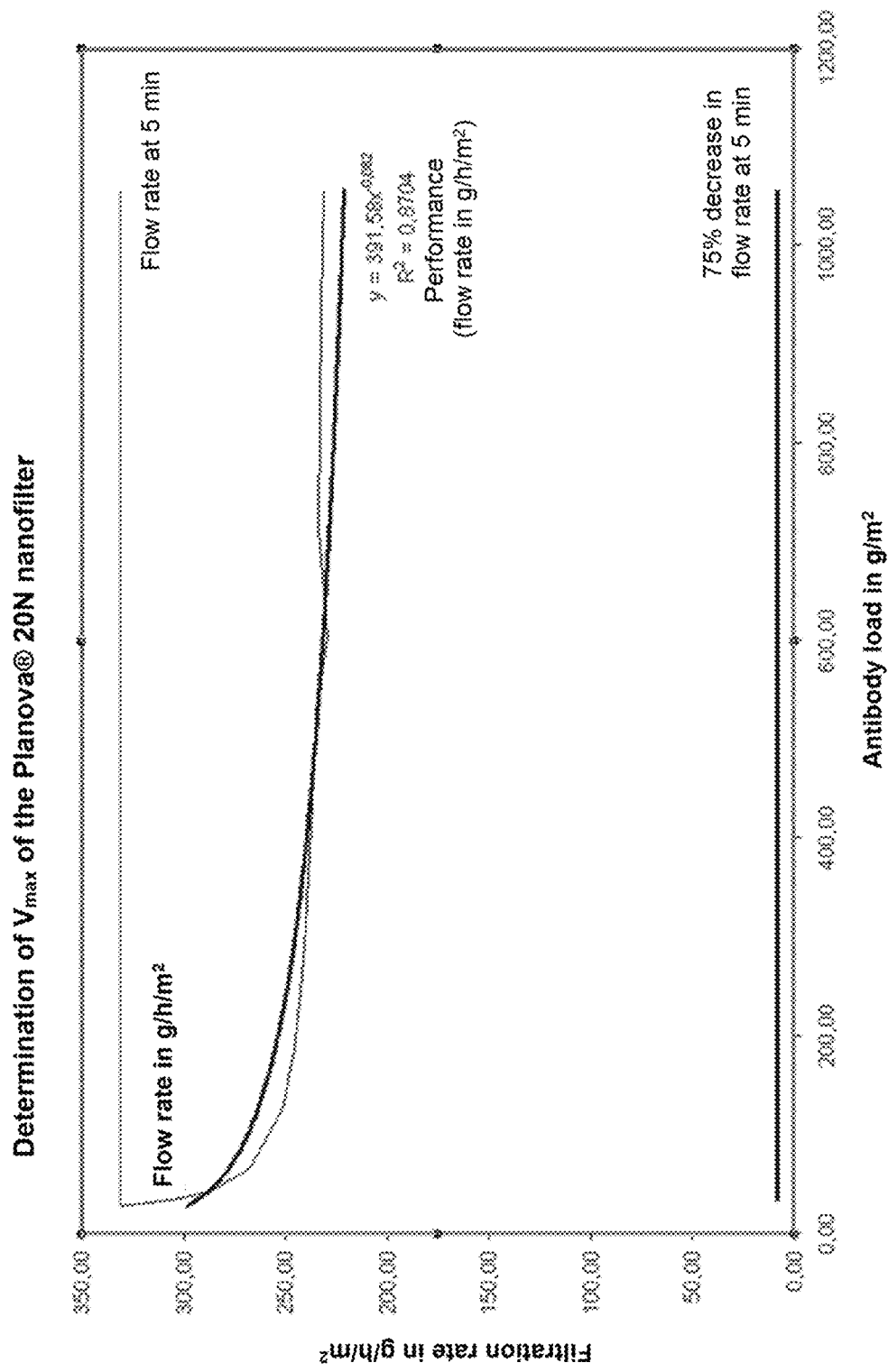

FIG. 4B represents filtration rate as a function of antibody load. The average rate was 0.8 mL/min for an antibody load ranging up to nearly 1100 g/m². The filtrate was clear at the end of the nanofiltration.

Nanofiltration on Viresolve® Pro 20N

Figure 4C:
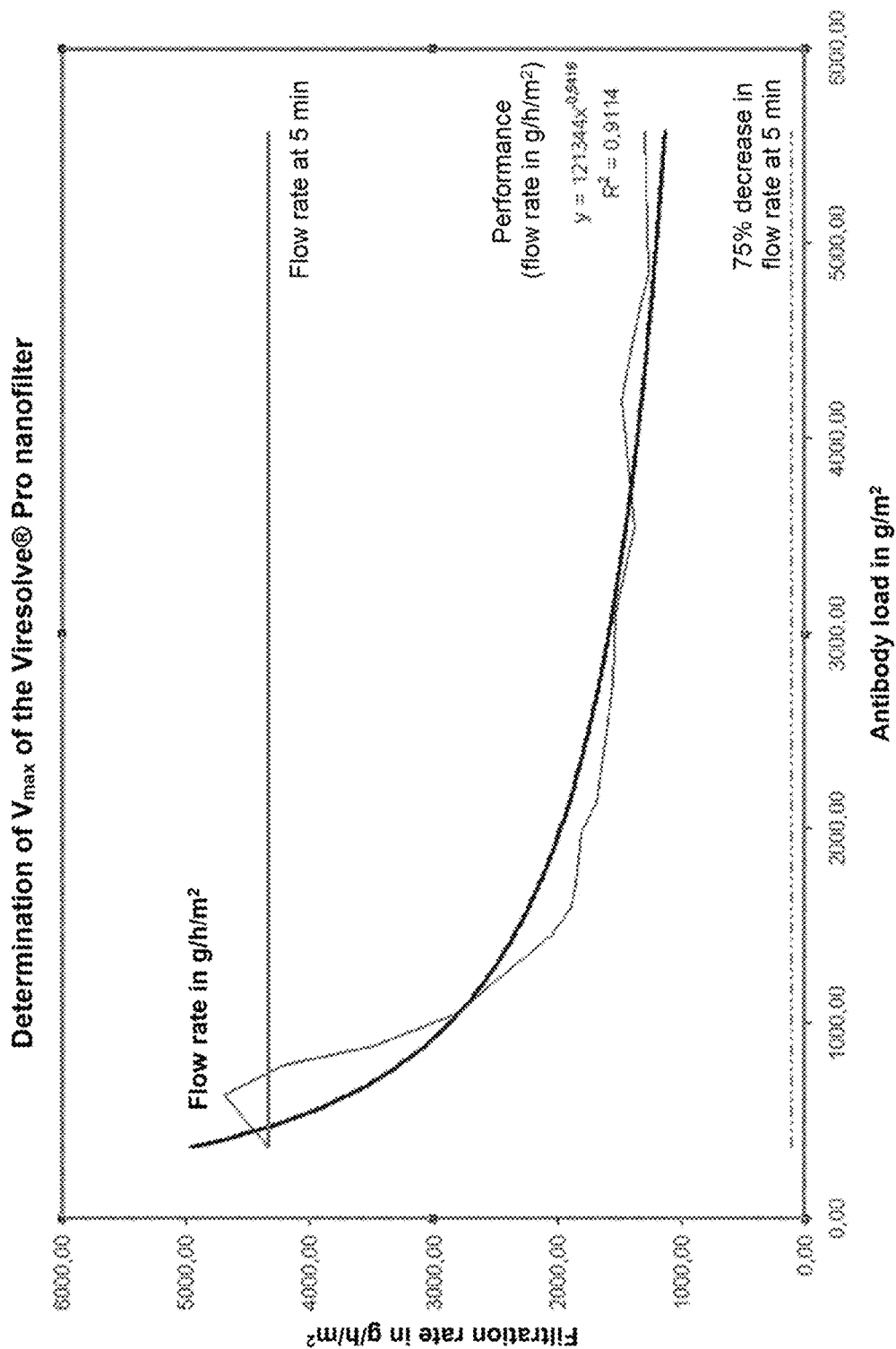

FIG. 4C represents filtration rate as a function of antibody load. The average rate was 2.4 mL/min for an antibody load ranging up to about 5500 g/m². The filtrate was clear at the end of the nanofiltration.

Comparison of Nanofiltered Antibody Load as a Function of Filtration Time

Figure 5:
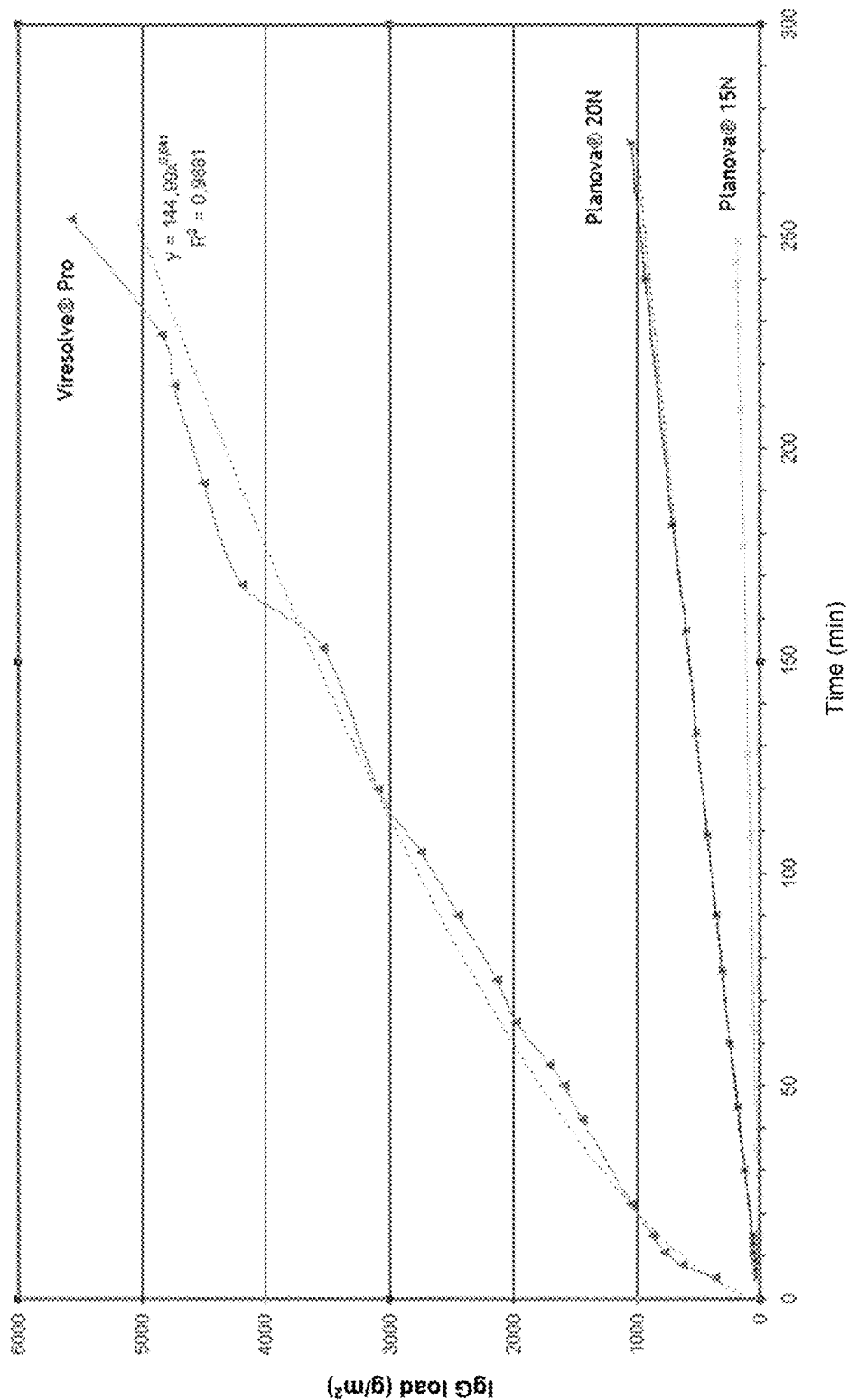
FIG. 5. Antibody load (g/m²) nanofiltered as a function of filtration time (minutes) for nanofiltration on a Planova® 15N, Planova® 20N or Viresolve® Pro 20N filter.

FIG. 5 represents nanofiltered antibody load as a function of filtration time, and very clearly illustrates the great superiority of the Viresolve® Pro 20N filter compared to the Planova® 15N and Planova® 20N filters.

By extrapolation, one would have after 4 hours:
Planova® 15N→200 g of IgG/m²
Planova® 20N→1000 g of IgG/m²
Viresolve® Pro+→5000 g of IgG/m²

Validation of the Use of the Viresolve Pro 20N Filter

Test 1

Clogging of the Viresolve® Pro+ filter is noted after 30 min. A load of 141 mg of product could thus be nanofiltered on 3.1 cm² of filter surface, or a quantity of antibody of 455 g/m² of nanofilter. This load is significantly lower than that obtained previously during the comparison of the three Planova® 15N, Planova® 20N and Viresolve® Pro+ filters 4865 g/m²).

Nevertheless, the decrease may be related to the characteristics of the filtered product (different from that filtered during the comparison of the three filters) and the maximum load remains much higher than that possible with the Planova® 15N filter.

Test 2

Clogging of the Viresolve® Pro filter is noted after 26.41 mL, or a quantity of 135.48 mg of antibody and a load of 437 g/m² of nanofilter. The load is about 300 g/m² at V75 and 425 g/m² at V90. The maximum load is similar to that obtained with test 1 and confirms the advantage of the Viresolve® Pro filter as compared to the Planova® filters. The purity of the nanofiltered product is determined by size-exclusion chromatography (HPSEC). It is estimated at 98.83% at this stage of the method.

Test 3

Filtration is stopped following the clogging of the nanofilter after 7.21 mL of product, or a quantity of 25.96 mg of antibody and a load of 84 g/m². This maximum load is much lower than those previously observed and illustrates a possible variability of the maximum load as a function of the state of the product to be nanofiltered. This variability justifies the test of use of a prefilter.

Use of a Prefilter

Direct Nanofiltration

Filtration is stopped following the clogging of the nanofilter after 7.21 mL of product, or a quantity of 25.96 mg of antibody and a load of 84 g/m².

Nanofiltration after Passing Through a Sartorius® Prefilter

Clogging of the prefilter is noted after 23.82 mL, or a quantity of 85.75 mg of filtered antibody and a load of 277 g/m². In this case, the load limit is imposed by the prefilter. The Sartorius® prefilter thus improves the maximum antibody load, but does not make it possible to restore a very high antibody load.

Nanofiltration after Passing Through a Millipore® Prefilter

Clogging of the prefilter is noted after 97 mL, or a quantity of 349.2 mg of antibody and a load of 1126 g/m². In this case, the load limit is imposed by the prefilter.

The Millipore® "OptiScale®-40 Viresolve® Prefilter" thus improves the maximum antibody load, making it possible to obtain a load higher than the already high load of the validation tests 1 and 2 described above with the Viresolve® Pro nanofilter alone.

Nanofiltration after Passing Through a Millipore® Prefilter (Validation on a $2^{nd}$ Product)

Clogging of the assembly is noted after 2 h 25 min after 193.2 mL has passed (at 3.23 g/L after 0.22 μm filtration), or a quantity of about 624 mg of antibody and a load of 2013 g/m². The assembly then is clamped and put on standby until the following day. After replacing the prefilter and resuming filtration, clogging of the assembly is noted after 24 min with 14.0 mL, or a quantity of 45.2 mg of antibody (load of 146 g/m²). The total load of the Viresolve® Pro+ solution is thus 2159 g/m². It should be noted that the destabilization of the product overnight does not make it possible to know if the prefilter or the filter is the source of this clogging.

In any case, this experiment validates the advantage of using a prefilter before nanofiltration on the Viresolve® Pro+ filter, to guarantee a very high antibody load.

Nanofiltration after Passing Through a Millipore® Prefilter (Validation on a $3^{rd}$ Product)

The 418.6 mL of product derived from the dialysis, or 938 mg (3 kg/m²), was nanofiltered in its entirety in 217 minutes with a final flow rate equivalent to 71.5% of the initial flow rate. The volume of nanofiltrate obtained was 407.5 mL at a concentration of 2.25 g/L, or 917 mg of proteins, which gives a step yield without rinsing of the nanofilter of 97.8%.

The assembly used made it possible to obtain a load of 2958 g/m², or a load 2.6 times higher than that of the first test and 1.4 times higher than that obtained with the $2^{nd}$ product.

Table Summarizing the Results Obtained

The various results obtained are summarized in Table 13 below:

Conclusions

The experiments carried out by the inventors clearly show the advantage of using a Viresolve® Pro filter for the nanofiltration of a purified antibody composition, in order to greatly increase the antibody load processed at one time and thus to significantly reduce the costs associated with this particularly expensive step.

Moreover, the addition of a prefilter makes it possible to further improve the antibody load processed at one time.

Overall, compared to a nanofiltration step using a Planova® 15N filter and an antibody load of 50 g/m² (prior method of the applicant), the modifications related to the selection of the Viresolve® Pro filter and the addition of a prefilter make it possible to obtain a more than 40-fold increase in load.

Example 4. Optimization of Impurity Removal During the Protein A Affinity Chromatography Step
a)

In order to optimize the removal of impurities during the protein A affinity chromatography step a), various conditions were tested on a new column with a resin based on methacrylate polymer in the form of beads having an average diameter of about 40-50 μm, on which is grafted a modified alkaline-stable C domain tetramer produced in *E. coli* (Amsphere™ Protein A A3 column, called "A3-JSR" hereafter). This column is particularly advantageous since it makes it possible to obtain eluates with a good yield, a low turbidity, and a good removal of impurities, particularly host cell proteins (HCP) and host cell DNA (HC-DNA) (see Tables 16 and 17 below), and this with a high load. Indeed, the value representing 90% of the $DBC_{10\%\ BT}$ of this column is 58 mg/mL.

Notably, various NaCl concentrations of the saline wash solution and various elution pH values were tested for the A3-JSR column (see Table 15 below).

The conditions tested for the A3-JSR column are summarized in Tables 14 and 15 below:

TABLE 13

Summary of the results obtained for the nanofiltration step e).

| Prefilter | Nanofilter | Antibody load | Comments |
|---|---|---|---|
| None | Planova ® 15N | 200 g/m² | Very low |
| None | Planova ® 20N | 1100 g/m² | Moderate |
| None | Viresolve ® Pro 20N | Comparison of 3 filters: 5500 g/m² Validation: Test 1: 455 g/m² Test 2: 437 g/m² Test 3: 84 g/m² | Potentially high, but highly variable, with clogging problems |
| Sartorius ® | Viresolve ® Pro 20N | 277 g/m² | Prefilter clogging |
| Millipore ® "OptiScale ®-40 Viresolve ® Prefilter" | Viresolve ® Pro 20N | Test 1 (1 prefilter): 1126 g/m² Test 2 (1 prefilter): 2159 g/m² Test 3 (2 prefliters in parallel): 2958 g/m² | Moderate to high, with limited variability |

TABLE 14

General conditions tested for the A3-JSR column.

| Designation | Solution/Buffer used | Residence time | Minimum volume of buffer/solution | Controlled parameters |
|---|---|---|---|---|
| Equilibration | 25 mM Tris, 5 mM EDTA, 25 mM NaCl buffer, pH 7.1 | 3 minutes | Until equilibration | pH and conduction |
| Injection | Filtered (0.2 μm), clarified culture supernatant | | 58 mg/mL of gel | OD at 280 nm |
| Return to baseline | 25 mM Tris, 5 mM EDTA, 25 mM NaCl buffer, pH 7.1 | | 4CV | NA |
| Wash (upflow flow reversal) | See Table 15 | | 4CV | NA |
| Return to baseline | 25 mM Tris, 5 mM EDTA, 25 mM NaCl buffer, pH 7.1 | | Until return to baseline | OD at 280 nm |
| Elution | 5 mM formate, 200 mM arginine buffer, pH see Table 15 | | 4CV | Collect at 250 mAU OD at 280 nm |

TABLE 15

Ionic strength of the wash solution and pH of the elution solution tested for the A3-JSR column.
A3-JSR
Load: 58 mg/mL of gel; Volume injected: 35 mL;
Residence time: 3 minutes; Flow rate: 0.6 mL/min

| Run no. | [NaCl] in the wash (mM) | Elution pH |
|---|---|---|
| 1A | 700 | 2.6 |
| 2A | 1200 | 3.94 |
| 3A | 1200 | 3.1 |
| 4A | 700 | 3.6 |
| 5A | 1200 | 3.1 |
| 6A | 700 | 3.6 |
| 7A | 1700 | 3.6 |
| 8A | 1700 | 2.6 |
| 9A | 2041 | 3.1 |
| 10A | 700 | 2.6 |
| 11A | 1200 | 3.1 |
| 12A | 1200 | 2.26 |
| 13A | 1200 | 3.1 |
| 14A | 1200 | 3.1 |
| 15A | 359 | 3.1 |
| 16A | 1700 | 3.6 |
| 17A | 1700 | 2.6 |

The results obtained just at the conclusion of the elution are summarized in Table 16 and those obtained after neutralization in Table 17 below:

TABLE 16

Results obtained just after elution, before neutralization.

| Run no. | [NaCl] in the wash (mM) | Elution pH | Elution volume | [Ig] | Q Ig | Yield | pH | Turbidity |
|---|---|---|---|---|---|---|---|---|
| 1A | 700 | 2.6 | 2.71 | 17.59 | 47.67 | 82.2% | / | 0.01 |
| 2A | 1200 | 3.94 | 9.99 | 3.82 | 38.16 | 65.8% | / | / |
| 3A | 1200 | 3.1 | NA | / | / | / | / | / |
| 4A | 700 | 3.6 | 4.06 | 12.13 | 49.25 | 84.9% | 4.88 | 0.016 |
| 5A | 1200 | 3.1 | 2.59 | 17.65 | 45.71 | 78.8% | 4.09 | 0.036 |
| 6A | 700 | 3.6 | 4.98 | 9.84 | 49.00 | 84.5% | 4.56 | 0.020 |
| 7A | 1700 | 3.6 | 4.68 | 10.69 | 50.03 | 86.3% | 4.57 | 0.022 |
| 8A | 1700 | 2.6 | 2.19 | 16.81 | 36.81 | 63.5% | 5.88 | 0.031 |
| 9A | 2041 | 3.1 | 2.58 | 18.3 | 47.21 | 81.4% | 4.07 | 0.051 |
| 10A | 700 | 2.6 | 3.41 | 16.81 | 57.32 | 98.8% | 3.58 | 0.095 |
| 11A | 1200 | 3.94 | 3.94 | 14.93 | 58.82 | 101.4% | 4.36 | 0.092 |
| 12A | 1200 | 2.26 | 4.04 | 14.18 | 57.29 | 98.8% | 2.81 | 0.114 |
| 13A | 1200 | 3.1 | 2.54 | 15.59 | 39.60 | 68.3% | 3.97 | 0.038 |
| 14A | 1200 | 3.1 | 2.63 | 18.01 | 47.37 | 81.7% | 4.01 | 0.011 |
| 15A | 359 | 3.1 | 2.5 | 18.93 | 47.33 | 81.6% | 4.03 | 0.012 |
| 16A | 1700 | 3.6 | 4.07 | 11.97 | 48.72 | 84.0% | 4.88 | 0.018 |
| 17A | 1700 | 2.6 | 2.66 | 16.01 | 42.59 | 73.4% | 3.05 | 0.023 |

TABLE 17

Results obtained after elution and neutralization.

| Run no. | [NaCl] in the wash (mM) | Elution pH | pH | Buffer volume | Turbidity | [Ig] | ng HCP/mg | Log HCP | pg DNA/mg | Log DNA |
|---|---|---|---|---|---|---|---|---|---|---|
| 1A | 700 | 2.6 | 6.03 | 50 | / | 10.08 | 57.6 | 3.8 | 933 | 3.2 |
| 2A | 1200 | 3.94 | 6.17 | 50 | / | 3.72 | 88.1 | 3.6 | 12166 | 2.0 |
| 3A | 1200 | 3.1 | / | / | Clear | | | | | |
| 4A | 700 | 3.6 | 6.34 | 10 | Slightly turbid | 6.93 | 84.3 | 3.6 | 603.2 | 3.4 |
| 5A | 1200 | 3.1 | 7.1 | 30 | Clear | 9.61 | 67.8 | 3.7 | 58 | 4.4 |
| 6A | 700 | 3.6 | 7.02 | 30 | Slightly turbid | 8.53 | 76.6 | 3.6 | 434.3 | 3.5 |
| 7A | 1700 | 3.6 | 6.47 | 15 | Slightly turbid | 8.79 | 92.5 | 3.6 | 12.5 | 5.0 |
| 8A | 1700 | 2.6 | 3.08 | 30 | Slightly turbid | 6.55 | 70.8 | 3.7 | 4.9 | 5.4 |
| 9A | 2041 | 3.1 | 6.55 | 20 | Turbid | 4.68 | 98.5 | 3.5 | 5874 | 2.4 |
| 10A | 700 | 2.6 | 6.04 | 80 | Turbid | 5.58 | 2000 | 2.2 | 28757 | 1.7 |
| 11A | 1200 | 3.1 | 6.43 | 60 | Turbid | 5.68 | 4900 | 1.8 | 9691 | 2.1 |
| 12A | 1200 | 2.26 | 6.84 | 250 | Slightly turbid | 4.55 | 1260 | 2.4 | 15187.7 | 1.9 |
| 13A | 1200 | 3.1 | 7.72 | 50 | | 3.8 | 114.7 | 3.5 | 245.16 | 3.7 |
| 14A | 1200 | 3.1 | 6.86 | 35 | Clear | 4.79 | 40.5 | 3.9 | 27.55 | 4.7 |
| 15A | 359 | 3.1 | 6.98 | 30 | Clear | 4.38 | 49.8 | 3.8 | 866.4 | 3.2 |
| 16A | 1700 | 3.6 | 6.5 | 20 | Slightly turbid | 4.28 | 44.2 | 3.9 | 11.45 | 5.1 |
| 17A | 1700 | 2.6 | 6.98 | 70 | Clear | 3.46 | 46.2 | 3.9 | 3 | 5.7 |

Figure 6:
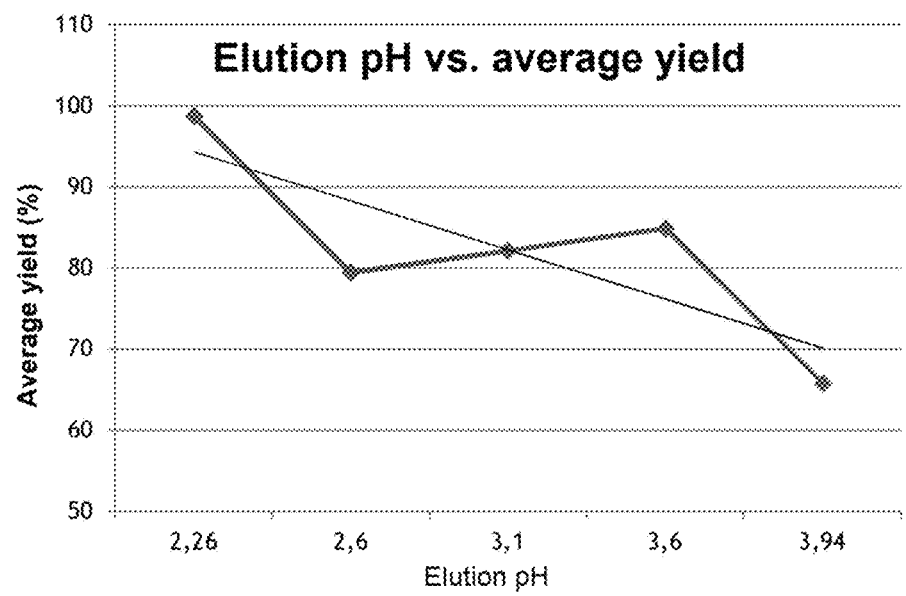
FIG. 6. Variation of average yield as a function of elution pH used for the A3-JSR column.

The variation of average yield as a function of elution pH used is represented in FIG. 6. Likewise, the variation of average HCP removal as a function of NaCl concentration in the wash solution and of elution pH are represented in FIGS. 7 and 8.

Figure 7:
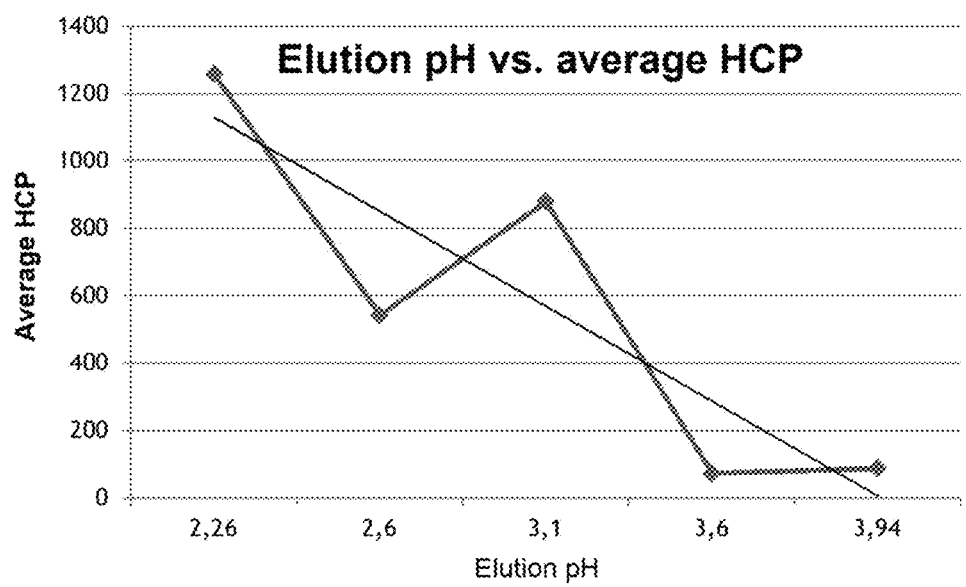
FIG. 7. Variation of average HCP removal as a function of elution pH used for the A3-JSR column.
Figure 8:
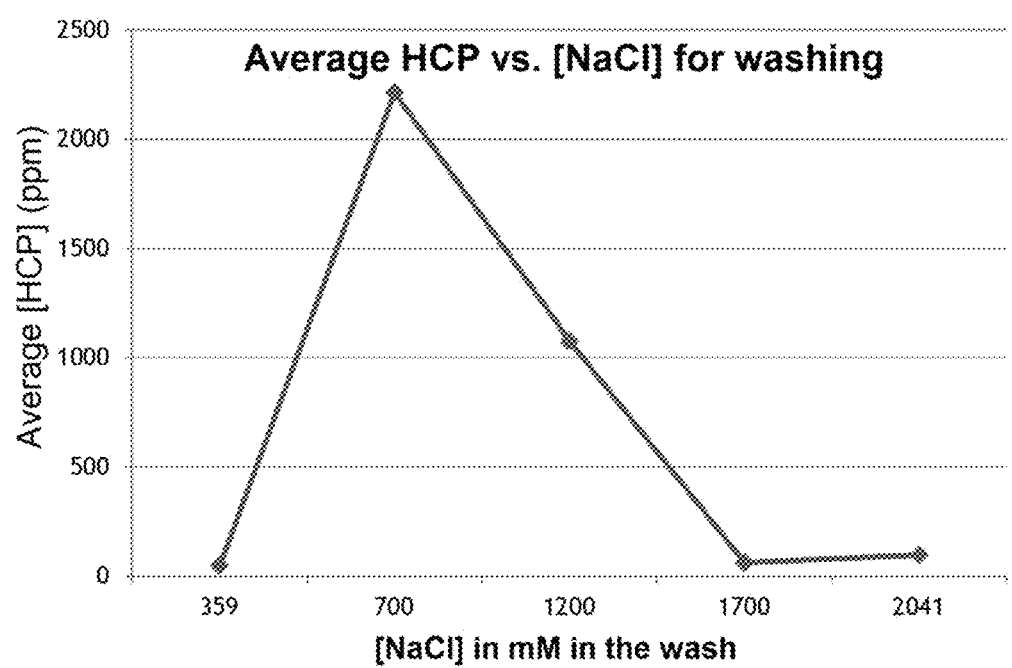
FIG. 8. Variation of average HCP removal as a function of NaCl concentration in the wash solution for the A3-JSR column.

The results presented in Tables 16 and 17 above and in FIGS. 6 to 8 show that the optimal yield conditions correspond to an elution pH of between 2.6 and 3.6, and that the optimal HCP removal conditions correspond to an elution pH of between 3.1 and 4 and to a wash solution comprising at least 1.2 M NaCl.

BIBLIOGRAPHICAL REFERENCES

Fahrner R L, Knudsen H L, Basey C D, Galan W, Feuerhelm D, Vanderlaan M, Blank G S. Industrial purification of pharmaceutical antibodies: development, operation, and validation of chromatography processes. Biotechnol Genet Eng Rev. 2001; 18:301-27.
Liu H F, Ma J, Winter C, Bayer R. Recovery and purification process development for monoclonal antibody production. MAbs. 2010 September-October; 2(5):480-99.
Edelman, G. M. et al., Proc. Natl. Acad. USA, 63, 78-85 (1969)
Kabat et al., Sequences of Proteins of Immunological Interest, 5th Ed. Public Health Service, National Institutes of Health, Bethesda, Md. (1991).
WO00/42072,
Shields R L, et al. J Biol Chem. 2001 Mar. 2; 276(9):6591-604.
Lazar, G. A., et al. Proc Natl Acad Sci USA. 103(11): 4005-10.
WO2004/029207
WO/2004063351
WO2004/074455
WO99/51642
WO2004074455A2
Idusogie E E et al. J Immunol. 2001; 166:2571-5.
Dall'Acqua et al. J Immunol 2006; 177:1129-1138.
Moore G L. Et al. mAbs 2:2, 181-189; March/April, 2010.
Verhoeyn et al. BioEssays, 8: 74, 1988.
Verhoeyen et al. Science, 239: 1534-1536, 1988.
Jones et al. Nature, 321: 522-525, 1986.
Riechmann et al. Nature, 332: 323-327, 1988.
Almagro et al. Frontiers in Bioscience 13, 1619-1633, Jan. 1, 2008.
Jakobovits et al., Proc. Natl. Acad. Sci. USA. 90:2551 (1993).
Jakobovits et al., Nature, 362:255-258 (1993).
Bruggermann et al., Year in Immuno., 7:33 (1993).
Duchosal et al. Nature 355:258 (1992) U.S. Pat. No. 5,591,669
U.S. Pat. No. 5,598,369
U.S. Pat. No. 5,545,806
U.S. Pat. No. 5,545,807
U.S. Pat. No. 6,150,584
Hoogenboom et al., J. Mol. Biol., 227:381 (1991).
Marks et al., J. Mol. Biol., 222:581-5 597 (1991).
Vaughan et al. Nature Biotech 14:309 (1996).
WO2012/041768
Manipulating the Mouse Embryo, A Laboratory Manual, Second edition, Cold Spring Harbor Laboratory Press (1994).
Gene Targeting, A Practical Approach, IRL Press at Oxford University Press (1993).
Ryan et aL, 1997 Science; 278: 873-876.
Cibelli et al., 1998 Science, 280: 1256-1258.
WO0026357A2
WO9004036A1
WO9517085A1
WO0126455A1
WO2004050847A2
WO2005033281A2
WO2007048077A2
WO0126455A1
WO2007106078A2

Stoger E, et al. Molecular Breeding 9: 149-158, 2002.
Fisher R, et al. Vaccine 21 (2003) 820-825.
Forthal et al, J Immunol 2010; 185; 6876-6882.
Ma J K, et al. Nat Rev Genet. 2003 October; 4(10):794-805.
Schillberg S, et al. Vaccine 23 (2005) 1764-1769.
U.S. Pat. No. 6,013,763
U.S. Pat. No. 5,084,559
U.S. Pat. No. 5,260,373
U.S. Pat. No. 6,399,750
U.S. Pat. No. 7,709,209
WO2012/083425
Löfdahl S, Guss B, Uhlén M, Philipson L, Lindberg M. Gene for staphylococcal protein A. Proc Natl Acad Sci USA. 1983 February; 80(3):697-701.
Uhlén M, Guss B, Nilsson B, Gatenbeck S, Philipson L, Lindberg M. Complete sequence of the staphylococcal gene encoding protein A. A gene evolved through multiple duplications. J Biol Chem. 1984 Feb. 10; 259(3): 1695-702.

The invention claimed is:

1. A method for purification of a monoclonal antibody or a fusion protein comprising a Fc fragment of an antibody and a second polypeptide from a sample, comprising:
   a) applying said sample comprising the monoclonal antibody or fusion protein to an affinity chromatography resin having as matrix a cross-linked methacrylate polymer gel, on which protein A is grafted, followed by eluting said monoclonal antibody or fusion protein with an elution buffer thereby obtaining a monoclonal antibody or fusion protein composition,
   b) inactivating viruses in the composition obtained from step a),
   c) applying the composition obtained from step b) to a cation-exchange chromatography resin having as matrix a cross-linked agarose gel, on which sulfonate groups ($-SO_3-$) are grafted via dextran-based spacer arms,
   d) subjecting the composition obtained from step c) to an anion-exchange chromatography step by applying said composition to a hydrophilic polyethersulfone membrane coated with a cross-linked polymer on which quaternary amine groups (Q) are grafted, and
   e) nanofiltering the composition obtained from step d) by applying said composition to a filter having a dual polyethersulfone membrane having a pore size of about 20 nm.

2. The method according to claim 1, wherein the cross-linked methacrylate polymer gel on which protein A is grafted used in step a) is in the form of beads having an average diameter of between 30 and 60 μm.

3. The method according to claim 1, wherein step a) comprises a sub-step of washing the resin with a saline solution comprising an NaCl concentration of at least 1 M.

4. The method according to claim 1, wherein the elution buffer used in step a) to elute the antibody is a formate buffer.

5. The method according to claim 4, wherein the formate buffer used for the elution of the antibody in step a) is used at a molarity of 5 to 10 mM and at a pH of between 2.6 and 3.6.

6. The method according to claim 1, wherein step b) is carried out by incubation for 30 to 120 minutes at a temperature of 20 to 25° C. in a medium comprising 0.5 to 2% (v/v) of polyoxyethylene-p-t-octylphenol (CAS no. 9002-93-1).

7. The method according to claim 1, wherein the membrane used during step d) is equilibrated with a trishydroxymethylaminomethane (TRIS) buffer at a concentration of 15 to 25 mM, a pH of 7.5 to 8.5 and a conductivity of 5 to 15 mS/cm.

8. The method according to claim 1, wherein step e) further comprises preliminary filtration through a depth filter comprising cellulose fibers, diatomaceous earth and a negatively-charged resin or a polyethersulfone membrane having a pore size of 0.22 μm functionalized by $SO_3^-$ groups.

9. The method according to claim 1, further comprising an ultrafiltration and/or diafiltration step.

10. The method according to claim 1, wherein the method is implemented on a culture supernatant of a clone producing the monoclonal antibody or the fusion protein comprising a Fc fragment of an antibody and a second polypeptide.

11. The method according to claim 1, for the purification of a monoclonal antibody.

12. The method according to claim 11, wherein the antibody is directed against one of the following antigens: Rhesus D, CD2, CD3, CD4, CD19, CD20, CD22, CD25, CD30, CD33, CD40, CD51 (Integrin alpha-V), CD52, CD80, CTLA-4 (CD152), SLAMF7 (CD319), Her2/neu, EGFR, EPCAM, CCR4, CEA, FR-alpha, GD2, GD3, HLA-DR, IGF1R (CD221), phosphatidylserine, TRAIL-R1, TRAIL-R2, *Clostridium difficile* antigens, *Staphylococcus aureus* antigens, cytomegalovirus antigens, *Escherichia coli* antigens, respiratory syncytial virus antigens, hepatitis B virus antigens, influenza virus A antigens, *Pseudomonas aeruginosa* serotype IATS O11 antigens, rabies virus antigens, or phosphatidylserine.

13. The method according to claim 2, wherein said beads have an average diameter of between 40 and 50 μm.

\* \* \* \* \*